(12) United States Patent
Schaser et al.

(10) Patent No.: US 11,154,653 B2
(45) Date of Patent: Oct. 26, 2021

(54) SYRINGE BARREL AND SYRINGE-CONFIRMATION ASSEMBLY

(71) Applicant: Illinois Tool Works Inc., Glenview, IL (US)

(72) Inventors: Robert Schaser, Algonquin, IL (US); Raymond Jozwik, Hendersonville, TN (US)

(73) Assignee: Illinois Tool Works Inc., Glenview, IL (US)

(*) Notice: Subject to any disclaimer, the term of this patent is extended or adjusted under 35 U.S.C. 154(b) by 197 days.

(21) Appl. No.: 15/988,464

(22) Filed: May 24, 2018

(65) Prior Publication Data

US 2018/0339103 A1 Nov. 29, 2018

Related U.S. Application Data

(60) Provisional application No. 62/510,290, filed on May 24, 2017.

(51) Int. Cl.
*A61M 5/00* (2006.01)
*A61M 5/145* (2006.01)
(Continued)

(52) U.S. Cl.
CPC .......... *A61M 5/007* (2013.01); *A61M 5/1407* (2013.01); *A61M 5/14546* (2013.01); *A61M 5/16804* (2013.01); *A61M 5/3129* (2013.01); *A61M 5/14566* (2013.01); *A61M 2205/0216* (2013.01); *A61M 2205/0272* (2013.01);
(Continued)

(58) Field of Classification Search
CPC ...... A61M 2205/14; A61M 2205/3306; A61M 2205/6063; A61M 2205/587; A61M 5/14546; A61M 5/14566; A61M 5/007; A61M 5/3129; A61M 5/3135

See application file for complete search history.

(56) References Cited

U.S. PATENT DOCUMENTS

| | | | |
|---|---|---|---|
| 8,439,876 B2 * | 5/2013 | Spohn | A61M 5/14566 604/131 |
| 2004/0064101 A1 * | 4/2004 | Kowan | A61M 5/14546 604/189 |
| 2017/0119962 A1 | 5/2017 | Fazi | |

FOREIGN PATENT DOCUMENTS

| | | |
|---|---|---|
| CN | 101391123 | 3/2009 |
| EP | 2243505 | 10/2010 |

OTHER PUBLICATIONS

International Search Report and Written Opinion for PCT/US2018/034405.

* cited by examiner

*Primary Examiner* — Shefali D Patel
*Assistant Examiner* — Avery Smale
(74) *Attorney, Agent, or Firm* — The Small Patent Law Group LLC; Joseph Butscher

(57) ABSTRACT

A syringe barrel includes a barrel body having a passage extending along a longitudinal axis between a tip opening and a load opening. The passage is configured to permit a plunger to advance therethrough along the longitudinal axis for driving a liquid through the tip opening. The barrel body includes a base portion that is configured to operably engage an injection system. The base portion has a body surface that is shaped to form a light-propagating space alongside the body surface. The light-propagating space extends to reflective ramps of the body surface. The reflective ramps have predetermined sizes and positions to reflect light signals radially away from the barrel body.

20 Claims, 16 Drawing Sheets

(51) Int. Cl.
  *A61M 5/168* (2006.01)
  *A61M 5/14* (2006.01)
  *A61M 5/31* (2006.01)
(52) U.S. Cl.
  CPC . *A61M 2205/3317* (2013.01); *A61M 2205/50* (2013.01); *A61M 2205/502* (2013.01); *A61M 2205/582* (2013.01); *A61M 2205/587* (2013.01); *A61M 2205/6063* (2013.01)

SYRINGE BARREL AND SYRINGE-CONFIRMATION ASSEMBLY

RELATED APPLICATIONS

The present application claims priority to U.S. Provisional Patent Application No. 62/510,290, entitled "Integrated Reflection Injection system," filed on May 24, 2017, which is incorporated herein by reference in its entirety.

The present application also claims priority to U.S. patent application Ser. Nos. 15/988,513 and 15/988,555, filed the same day as the present application, each of which is incorporated herein by reference in its entirety.

FIELD OF EMBODIMENTS OF THE DISCLOSURE

Embodiments of the present disclosure generally relate to an injection system that injects a fluid into a patient during a medical procedure and components of the injection system.

BACKGROUND

Various medical procedures supply a designated fluid to a patient in a controlled manner. Examples include saline, drug delivery, and contrast media. Contrast media is injected into a patient for diagnostic and therapeutic imaging procedures, such as computed tomography (CT). The contrast media is typically delivered at a predetermined rate or schedule and at relatively high pressures.

Powered injection systems are often used during such procedures. U.S. Pat. No. 6,652,489 discloses a front-loading powered injection system, syringes, syringe interfaces, syringe adapters, and syringe plungers. These injection systems can be programmed to, among other things, deliver the fluid at a predetermined rate or schedule and can provide the fluid at the designated pressure.

Such injection systems, however, may have one or more problems. For example, at least one known injection system is automatically activated when the syringe is inserted within a port of the injection system and operably engaged to the injection system. The injection system uses a light detector to confirm the presence of the syringe and, optionally, other information about the syringe. Light is directed through the wall of the syringe and refracted by grooves along an outer surface of the wall. The refraction generates light signals that are read by the light detector. The light signals confirm the presence of the syringe within the port and may provide additional information about the syringe (e.g., fluid contained within the syringe). This known system, however, may generate several errors or misreadings.

The light is directed through the walls when a sensor is triggered by the syringe. A flex ring is positioned within a housing at an interface of the port. A portion of the syringe is inserted through the flex ring. As the syringe is inserted to secure the syringe to the injection reader, a flange that projects radially outward from the syringe engages the flex ring, thereby moving the flex ring. When the flex ring moves, a hall-effect sensor within the interface is triggered. In response to this trigger, the injection system prepares for operation and the piston engages the plunger.

In this known system, however, it is necessary for the syringe to engage the flex ring each time the syringe is loaded, thereby causing wear and requiring frequent replacement of the flex ring. Moreover, the injection system automatically prepares itself when the syringe is loaded, which may not be desirable in some cases.

In addition to the above, a significant amount of pressure is applied to the fluid within the syringe which may cause the liquid to leak. As such, the side of the injection system that supports the syringe is exposed to liquid. The liquid may damage the injection reader or may possibly be a health risk to individuals who come in contact with the liquid.

SUMMARY OF EMBODIMENTS OF THE DISCLOSURE

In accordance with one or more embodiments, a syringe barrel is provided. The syringe barrel comprises a barrel body that has a passage extending along a longitudinal axis between a tip opening and a load opening. The passage is configured to permit a plunger to advance therethrough along the longitudinal axis for driving liquid through the tip opening. The barrel body includes a base portion that is configured to operably engage an injection system. The base portion has a body surface that is shaped to form a light-propagating space alongside the body surface. The light-propagating space is defined by reflective ramps of the body surface. The reflective ramps have predetermined sizes and positions to reflect light signals radially away from the barrel body.

In some aspects, the light-propagating space may include a light-propagating recess defined between side surfaces.

In some aspects, the base portion may have a load edge that may define the load opening. The load edge may have a reduced thickness along the light-propagating recess. The light-propagating recess may extend from the load edge to the reflective ramps.

In some aspects, the body surface may be an exterior surface.

In some aspects, the base portion may include a base wall that may have the body surface and a load edge that may define the load opening. The base portion may be incapable of having an appreciable amount of electromagnetic radiation with a detectable wavelength propagate from the load edge through the base wall to the reflective ramps. Optionally, the base portion may be incapable of having the appreciable amount of electromagnetic radiation with a detectable wavelength propagate from the load edge through the base wall to the reflective ramps because of at least one of the following (a) the base portion is shaped from an opaque material; (b) the body surface of the base portion is coated with an opaque material; or (c) the base portion includes discontinuities therein that scatter the electromagnetic radiation.

In some aspects, the light-propagating space may be defined by at least first and second levels of the body surface.

In some aspects, the light-propagating space may be a first light-propagating space and the reflective ramps may be first reflective ramps. The barrel body may be shaped to form a second light-propagating space that may be defined between the end of the base portion and second reflective ramps. The second reflective ramps may have predetermined sizes and positions to reflect light signals radially away from the barrel body. The first and second light-propagating spaces may be located on opposite sides of the barrel body or on opposite sides of a wall of the barrel body.

In some aspects, the barrel body may include a main portion. The main portion and the base portion may be discrete elements that may be attached to each other to form the barrel body. Optionally, the syringe barrel may comprise one of the main portion or the base portion that may have an edge channel that may extend circumferentially around the longitudinal axis and may open in a direction along the longitudinal axis. The edge channel may be defined between an inner wall and an outer wall. The other of the main portion or the base portion may have an edge track that may extend circumferentially around the longitudinal axis. The edge track may be configured to be received within the edge channel and may threadably engage each other such that the edge track may be secured between the inner wall and the outer wall that define the edge channel.

In accordance with one or more embodiments, an assembly is provided. The assembly comprises a syringe barrel that has a passage extending along a longitudinal axis between a tip opening and a load opening. The passage is configured to permit a plunger to advance therethrough along the longitudinal axis for driving liquid through the tip opening. The syringe barrel includes a base portion that is configured to operably engage an injection system. The base portion has a body surface that is shaped to form a light-propagating space alongside the base portion. A light source is configured to generate light. The light source is positioned to direct light through the light-propagating space alongside the body surface. The base portion includes reflective ramps. The reflective ramps have predetermined sizes and positions to reflect light signals radially away from the syringe barrel. The light is electromagnetic radiation and may have a designated wavelength or a designated range of wavelengths.

In some aspects, the light-propagating space may include a light-propagating recess that may be defined between side surfaces that may partially oppose each other with the light-propagating space therebetween.

In some aspects, the base portion may have a load edge that mat define the load opening. The load edge may have a reduced thickness along the light-propagating recess.

In some aspects, the light-propagating space may be defined by at least first and second levels of the body surface. The base portion may include a base wall that may have the body surface and a load edge that may define the load opening.

In some aspects, the base portion may be incapable of having an appreciable amount of electromagnetic radiation with a detectable wavelength propagate from the load edge through the base wall to the reflective ramps. For example, the base portion may be incapable of having the appreciable amount of electromagnetic radiation with the detectable wavelength propagate from the load edge through the base wall to the reflective ramps because of at least one of the following: (a) the base portion is shaped from an opaque material; (b) the body surface of the base portion is coated with an opaque material; or (c) the base portion includes discontinuities therein that scatter the electromagnetic radiation.

In some aspects, the light-propagating space may be a first light-propagating space and the reflective ramps may be first reflective ramps. The syringe barrel may be shaped to form a second light-propagating space that may extend to second reflective ramps. The second reflective ramps may have predetermined sizes and positions to reflect light signals radially away from the syringe barrel.

In some aspects, the syringe barrel may also include a main portion. The main portion and the base portion may be discrete elements that may be attached to each other to form the syringe barrel.

In accordance with one or more embodiments, an injection system is provided. The injection system comprises an injector head that is configured to control delivery of a designated fluid to a patient. The injector head includes a syringe interface along an active side of the injector head. The syringe interface has a receiving cavity that is configured to receive a syringe barrel. The injector head also includes an internal sensor. A magnetic switch has an external magnet outside of the injector head. The external magnet is operable to modify a magnetic field experienced by the internal sensor to activate the internal sensor.

In some aspects, the injector head also includes an internal movable magnet that may be operable to move relative to the internal sensor when a syringe barrel is inserted into the receiving cavity. The magnetic field experienced by the internal sensor may be a function of respective magnetic fields produced by the movable magnet and the external magnet.

In some aspects, each of the magnetic switch and the movable magnet may be capable of independently activating the internal sensor.

In some aspects, the respective magnetic field of the magnetic switch may reduce an effect of the respective magnetic field of the movable magnet on the internal sensor. Optionally, the internal sensor may be within three centimeters from the receiving cavity and may be within three centimeters of an exterior of the injector head. The external magnet may include an electromagnet that may be configured to selectively produce a respective magnetic field.

In some aspects, the electromagnet may be located alongside the active side of the injector head. The external magnet may include a permanent magnet. The permanent magnet may be configured to be moved between different positions, thereby moving the respective magnetic field of the permanent magnet. The permanent magnet may be operable to move alongside the active side of the injector head.

In some aspects, the injection system may comprise a side cover that may cover at least a portion of the active side. Optionally, the side cover may include a track that is slidably coupled to the e magnet. The permanent magnet may slide along the track between the different positions. The permanent magnet may move relative to the internal sensor as the permanent magnet moves along the track. The side cover may include at least one of a shroud or a fascia.

In accordance with one or more embodiments, an injection sub-assembly is provided. The injection sub-assembly comprises a support structure that is configured to be coupled to an injector head for controlling delivery of a designated fluid to a patient. An external magnet is coupled to the support structure outside of the injector head. The external magnet is operable to modify a magnetic field experienced by the internal sensor to activate the internal sensor.

In some aspects, the external magnet may include an electromagnet that may be configured to selectively produce a respective magnetic field.

In some aspects, the external magnet may include a permanent magnet that may be configured to be moved between different positions, thereby moving the respective magnetic field of the permanent magnet. The permanent magnet may be operable to move alongside the active side of the injector head.

In some aspects, the injection sub-assembly may also include a side cover that may include or forms the support structure. The side cover may have a syringe opening and may be configured to be mounted to an active side of the injector head.

In accordance with one or more embodiments, a method is provided. The method comprises providing an injector head configured to control delivery of a designated fluid to a patient. The injector head includes a syringe interface along an active side of the injector head. The syringe interface has a receiving cavity that is configured to receive a syringe barrel. The injector head also includes an internal sensor. Actuating a magnetic switch has an external magnet outside of the injector head. In response to being actuated, the magnetic switch generates a respective magnetic field to modify a magnetic field experienced by the internal sensor.

In some aspects, the injector head may also include an internal movable magnet that may be operable to move relative to the internal sensor when a syringe barrel is inserted into the receiving cavity. The magnetic field experienced by the internal sensor may be a function of respective magnetic fields produced by the movable magnet and the external magnet.

In some aspects, each of the magnetic switch and the movable magnet may be capable of independently activating the internal sensor.

In accordance with one or more embodiments, an injection system is provided. The injection system comprises an injector head that is configured to control delivery of a designated fluid to a patient. The injector head includes a syringe interface along an active side of the injector head. The syringe interface has a receiving cavity that is configured to receive a syringe barrel. A side cover has a syringe opening therethrough. The side cover is sized and shaped to cover at least a portion of the active side of the injector head such that the receiving cavity and the syringe opening align with each other to form a port that receives the syringe barrel.

In some aspects, the injector head may be part of a legacy system that may be operable without the side cover. For example, the legacy system has been used for delivering liquids. The legacy system is capable of operating without the side cover.

In some aspects, the side cover may be removably mounted to the injector head.

In some aspects, the side cover may have a deflectable rib with a radially-inward surface that may define a portion of the port. Optionally, the deflectable rib may have a radially-outward surface defining a tactile opening. The deflectable rib may move when engaged with the syringe barrel such that a size or shape of the tactile opening may change when the deflectable rib moves. Optionally, the side cover may include a shroud and a fascia that may have the tactile opening.

In some aspects, the shroud may be sized and shaped to cover the tactile opening. For example, the shroud may cover at least 90% of an exterior surface of the fascia. Optionally, the side cover may include a fascia that may cover at least a portion of the active side and a shroud that may cover at least a portion of the fascia.

In some aspects, the fascia may include a secondary opening and the syringe opening. The shroud may cover the secondary opening but not the syringe opening. The fascia and the cover may be stacked side-by-side and may be secured to each other.

Optionally, the injection system may further comprise a strap. The fascia and the cover may be secured to each other by the strap. Optionally, the side cover may cover at least 90% of an exterior surface of the active side.

In some aspects, the injection system may also include an external magnet that may be coupled to the side cover. The external magnet may be at least one of (a) a permanent magnet operable to move with respect to the injector head or (b) an electromagnet.

Optionally, the side cover may include a fascia that may cover at least a portion of the active side and a shroud that may cover at least a portion of the fascia. At least one of the fascia and the shroud may have a respective slot that may receive the external magnet. The external magnet may be movable within the respective slot.

In accordance with one or more embodiments, an injection system is provided. The injection system comprises a syringe barrel that has a passage extending along a longitudinal axis between a tip opening and a load opening of the syringe barrel. An injector head is configured to control delivery of a designated fluid to a patient. The injector head includes a syringe interface along an active side of the injector head. The syringe interface has a receiving cavity configured to receive a syringe barrel. A side cover has a syringe opening therethrough. The side cover is sized and shaped to cover at least a portion of the active side of the injector head such that the receiving cavity and the syringe opening align with each other to form a port that receives the syringe barrel. The syringe barrel is configured to rotate an operating turn between a start position and a loaded position. The syringe barrel is releasable when in the start position. The side cover has a radially-inward surface that defines a portion of the syringe opening. The radially-inward surface and the syringe barrel are shaped relative to each other such that the radially-inward surface and the syringe barrel slidably engage each other during the operating turn. The radially-inward surface and the syringe barrel are shaped relative to each other such that a torque for rotating the syringe barrel from the start position and from the loaded position is less than the torque for rotating the syringe barrel between the start and loaded positions.

In some aspects, the side cover may include a deflectable or compressible physical feature that may include the radially-inward surface.

In some aspects, the side cover may be removable.

In some aspects, the side cover may include a lip that may extend around a majority of a perimeter of the side cover.

In accordance with one or more embodiments, a method is provided. The method comprises providing an injector head that is configured to control delivery of a designated fluid to a patient. The injector head includes a syringe interface along an active side of the injector head. The syringe interface has a receiving cavity. The method inserts a syringe barrel into the receiving cavity of the syringe interface operably engages the injector head and the syringe barrel. The method also includes operably engaging the injector head.

In some aspects, operably engaging the injector head and the syringe barrel includes rotating the syringe about an operating turn between a start position and a loaded position. A torque may rotate the syringe barrel from the start position and from the loaded position may be less than the torque for rotating the syringe barrel between the start and loaded positions.

In at least one embodiment, the syringe barrel includes a barrel body having a passage extending along a longitudinal axis between a tip opening and a load opening. The passage is configured to permit a plunger to advance therethrough for driving liquid through the tip opening. The barrel body includes a main portion and a base portion that are discrete elements and configured to be rotatably coupled to each other. One of the main portion or the base portion has an edge channel that extends circumferentially around the longitudinal axis and opens in a direction along the longitudinal axis. The edge channel is defined between an inner wall and an outer wall. The other of the main portion or the base portion has an edge track that extends circumferentially around the longitudinal axis. The edge track is configured to be received within the edge channel and threadably engage each other such that the edge track is secured between the inner wall and the outer wall that define the edge channel.

In some aspects, the edge track has an inward-facing surface and the inner wall has an outward-facing surface. The inward-facing surface and the outward-facing surface are tapered in a direction toward the longitudinal axis. Optionally, an inner ring structure is coupled to the inner wall. Optionally, the inner ring structure projects from a top of the inner wall.

In some aspects, the inner ring structure is coupled to the inner wall and extends circumferentially around the longitudinal axis and projects radially-inward from the inner wall.

In some aspects, the main portion and the base portion have respective bosses that engage each other as the main portion and the base portion reach a fully-engaged condition. The bosses provide a positive stop that indicates that the main portion and the base portion are in the fully engaged condition.

In some aspects, the base portion has a body surface that is shaped to form a light-propagating space alongside the body surface. The light-propagating space is defined between an end of the base portion and reflective ramps of the body surface. The reflective ramps have predetermined sizes and positions to reflect light signals radially away from the barrel body.

In accordance with one or more embodiments, an injection sub-assembly is provided that includes a side cover having a syringe opening. The side cover is configured to be mounted to an active side of an injector head for controlling delivery of a designated fluid to a patient. The injection sub-assembly also includes an external magnet coupled to the side cover outside of the injector head. The external magnet is operable to modify a magnetic field experienced by an internal sensor within the injector head to activate the internal sensor.

Figure 2:
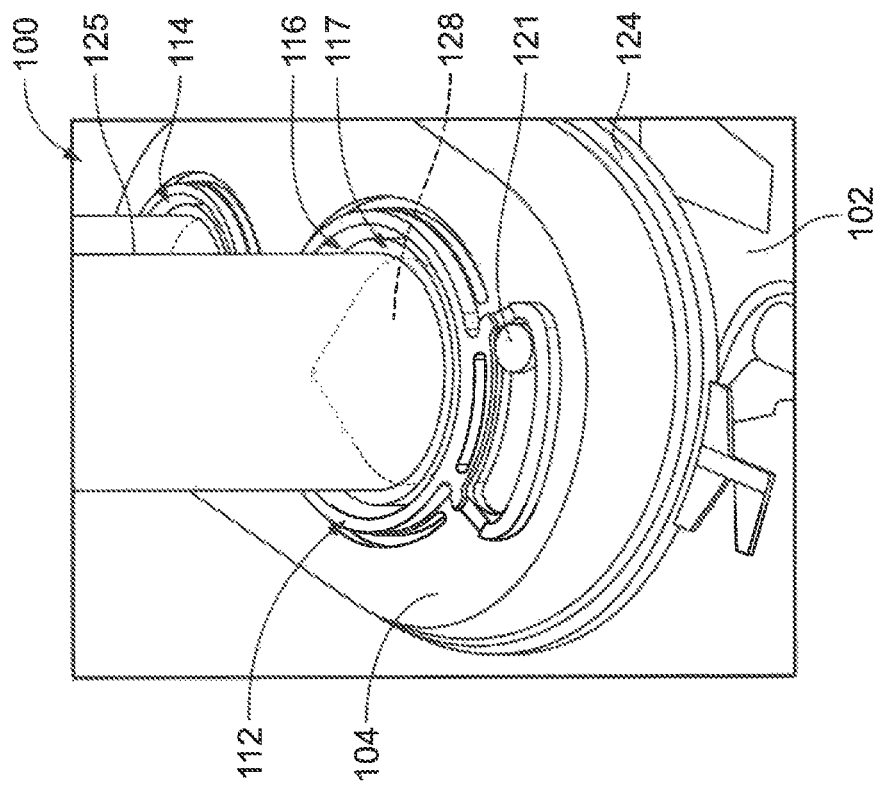
FIG. 2 is a top perspective view of the injection system of FIG. 1 having a syringe barrel received in one port of the injection system.

Before the embodiments of the disclosure are explained in detail, it is to be understood that the disclosure is not limited in its application to the details of construction and the arrangement of the components set forth in the following description or illustrated in the drawings. The disclosure is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF EMBODIMENTS OF THE DISCLOSURE

Embodiments set forth herein may include injection systems, fascias for such systems, system barrels, and methods of making and using the same. Embodiments may be used while injecting a designated fluid, such as a contrast media or saline, into a patient prior to and/or during a medical procedure (e.g., CT scan). Embodiments may include a syringe barrel (e.g., a 200 ml syringe barrel) having a base portion and a main portion that are manufactured separately and then assembled together. In certain embodiments, the base portion includes surfaces that have a refractive index configured to reflect light signals propagating from a light source. The base portion may comprise an opaque material. Unlike prior known systems that rely on refraction, the syringe barrel is configured to activate a light sensor circuit in the injector head through reflection.

The fascia may be a multi-purpose fascia. In the illustrated embodiment, the fascia is configured to (a) protect the injector head from leaked fluid; (b) support a mechanism (e.g., switch) for activating or initiating the injector head; and (c) provide a tactile indication to a user that the syringe barrel has been moved to a loaded position or has been moved to a start/releasable position. In other embodiments, the fascia may be configured any one of (a), (b), or (c) or any two of (a), (b), or (c).

Embodiments may reduce wear on components and may be less susceptible to spillage and/or leakage as compared to prior known systems. For instance, the fascias and syringe barrels described herein may reduce the frequency for replacing a flex ring and/or reduce the likelihood that liquid will leak from the syringe barrel and spill on the injector head. The syringe barrels may also enhance user experience by being identified/read more consistently. The fascia may enhance user experience by providing a tactile indication that the syringe barrel has been loaded onto the injector head or the syringe barrel is releasable from the injector head.

Figure 1:
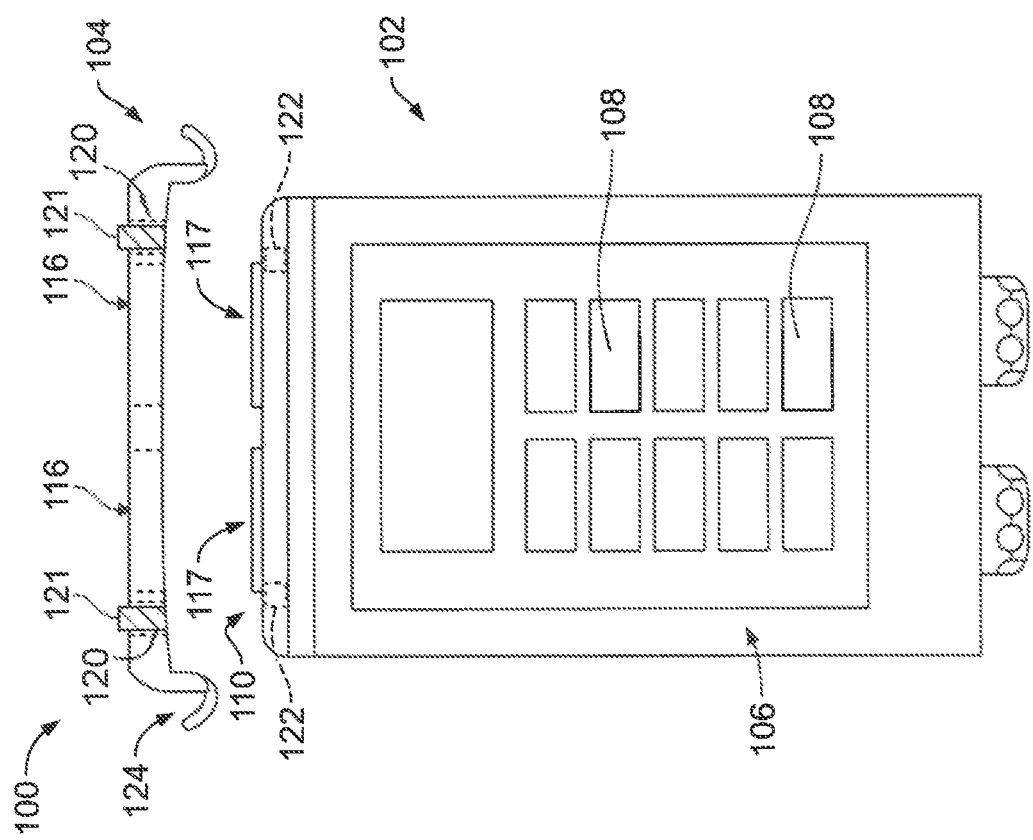
FIG. 1 is a side view of an injection system formed in accordance with an embodiment that includes a known injector head and a fascia.

FIG. 1 is a side view of an injection system 100 that includes an injector head 102 and a fascia 104, which may also be referred to as a side cover in some embodiments. FIG. 2 is an enlarged view of the injection system 100 having the fascia 104 coupled to the injector head 102. The injection system 100 is a flow-control system that adjusts operation of a piston (not shown) for controlling a flow rate of liquid that is delivered by the injection system 100. The injection system 100 is configured to support one or more syringe barrels 125 and inject a designated fluid into a patient (e.g., human or animal) through the syringe barrels 125. For example, the injector head 102 may include linearly reciprocal pistons that each engage a plunger 128 (FIG. 2) disposed within a syringe barrel 125.

In some embodiments, the injector head 102 may be a known injector head. In particular embodiments, the injection system 100 is configured to inject intravenous contrast media and saline into patients for diagnostic studies in computed tomography (CT) applications. It should be understood, however, that the injection system 100 may be used in other medical procedures.

In some embodiments, the fascia 104 may be removably coupled to the injector head 102 such that the fascia 104 may be attached and detached from the injector head 102 without damaging the injector head 102 or the fascia 104. The fascia 104 may cover at least a portion of an active side 110 (FIG. 1) of the injector head 102. In the illustrated embodiment, the fascia 104 is sized and shaped to cover the entire active side 110 and includes a peripheral lip 124 extending around at least a majority of a perimeter of the fascia 104. The peripheral lip 124 is designed to reduce the likelihood that leaked liquid will directly contact the injector head 102. Optionally, the fascia 104 may be configured to cover more than one side of the injector head 102 or less than the entire active side 110.

The injector head 102 includes a user interface 106 having an array of user-activated control elements 108, which may include physical elements (e.g., switches, buttons, knobs) and/or virtual elements (e.g., buttons appearing on a touch-screen). The user-activated control elements 108 may enable a user to, for example, selectively control a flow rate of the fluid, selectively control a temperature of the delivered fluid, or purge air within the injection system or syringe barrel. Although not shown, the injection system 100 may be part of a larger system that includes a computing system, display, and a pedestal or stand for holding the injection system 100.

The active side 110 is configured to receive the fascia 104. In the illustrated embodiment, the injection system 100 includes ports 112, 114. Each of the ports 112, 114 is configured to receive one of the syringe barrels 125. The syringe barrel 125 is configured to be front-loaded such that a base portion of the syringe barrel 125 is inserted through the corresponding port. Each of the ports 112, 114 includes an opening 116 through the fascia 104 and a receiving cavity 117 of the injector head 102.

As described herein, the fascia 104 may include a magnetic switch 120 that is positioned adjacent to a sensor 122 (e.g., Hall Effect Sensor) of the injector head 102 such that the magnetic switch 120 is capable of activating the sensor 122. The magnetic switch 120 may include a permanent magnet 121. In other embodiments, the magnetic switch 120 may include an electromagnet. The magnetic switch and the permanent magnet 121 is positioned outside of the injector head 102 in the illustrated embodiment. For example, the permanent magnet 121 may be immediately adjacent to the injector head 102 such that the permanent magnet 121 engages the injector head or has only a nominal gap therebetween (e.g., less than 5 millimeters).

The permanent magnet 121 is operable to modify a magnetic field experienced by the internal sensor to activate the internal sensor. In the illustrated embodiment, the permanent magnet 121 is bobbin-shaped or barbell-shaped and forms a snap-fit with the fascia 104. The sensor 122 is identified by dashed lines in FIG. 1. The sensor 122 is triggered in response to the magnetic switch 120 being activated (e.g., moved by a user). More specifically, the permanent magnet 121 and the corresponding magnetic field of the permanent magnet 121 may move relative to the sensor 122. The injector head 102 may execute one or more operations in response to the sensor 122 being triggered. For example, the injector head 102 may identify/read the syringe barrel 125 and/or move a piston (not shown) to prepare for injecting the designated fluid into the patient. In response to the sensor 122 being triggered, the injector head 102 may automatically retract or automatically advance a piston into the passage of the syringe barrel.

FIGS. 3-6 illustrate a known injector sub-assembly 200 that includes a known syringe interface 202 and a known syringe 204. As described herein, the syringe 204 may be replaced by the syringe barrel 125. The syringe interface 202 may be considered a portion of the injector head 102 and is configured to couple the syringe 204 to the injector head 102. The syringe interface 202 provides a mechanism by which a syringe (or syringe barrel) may be seated quickly relative to an injector head 102. A rear surface 206 of the syringe interface 202 attaches to a front surface 208 of injector head 102. A front surface 220 of syringe interface 202 is adapted to receive a rear end 222 of syringe 204.

The syringe interface 202 includes a connector housing 224 and a flex ring 226, which is disposed within the connector housing 224 near a front surface 220. The syringe 204 includes a cylindrical body 230 with a tapering conical portion 232 at a front end 234. The conical portion 232 is integrally connected to a discharge end 236. The discharge end 236 is provided with a luer lock 238 that may be connected to a tube (not shown) that is connected ultimately to the patient (also not shown).

A ridge 244 is integrally formed on the syringe 204 toward rear end 222 of syringe 204. In the illustrated embodiment, the ridge 244 is formed to be continuous around the perimeter of syringe 204. The ridge 244 includes two parts, a sloping section 246 and a shoulder section 248 that is essentially perpendicular to the exterior surface of cylindrical body 230. Two or more extending tabs 250 provided forward of shoulder 248, between shoulder 248 and flange 242. Tabs 250 are configured to engage flex ring 226 to release syringe 204 from connection with syringe interface 202. As described herein, the syringe barrel 125 (FIG. 2) and other syringe barrels do not include a tab that engages the flex ring and are not designed to engage the flex ring.

The front plate 254 has a hole 258 therethrough. A lip 260 extends around the periphery of the hole 258. When syringe 204 engages syringe interface 202, the flange 242 and the lip 260 with one another to minimize any leaked contrast medium from entering the interior of syringe interface 202 through hole 258. Alternatively, syringe 204 may be constructed so that it does not include flange 242. Flange 242 can also, however, serve an additional function as a mechanical stop when it engages with front surface 220 of front plate 254, ensuring proper axial positioning of syringe 204 with respect to injector head 102.

The flex ring 226 may be made from an acetal copolymer or any other suitable material. The flex ring 226 can include, on either side, a linear or flattened portion 262 that is integrally connected to two curved portions 264. As shown, flex ring 226 includes a 258 therethrough. On a front side of flex ring 226, one or more chamfered surfaces 282 can be provided to facilitate insertion of rear end 222 and ridge 244 of syringe 204 therethrough.

A rear surface 296 of front plate 254 includes an indentation or recess 298 that has a shape similar to flex ring 226. Two notches 299 are formed in rear surface 296 of front plate 254. Notches 299 accommodate extensions 268 of flex ring 226. Indentation 298 is shaped to be larger than flex ring 226 and a distance between notches 299 is greater than a distance between extension 268 when flex ring 226 is in a relaxed state. Notches 299 help to prevent flex ring 226 from rotating within housing 224, while permitting flex ring 226 to expand to its extended state.

To connect syringe 204 to syringe interface 202, rear end 222 of syringe 204 is inserted into connector housing 224 through hole 258 in front plate 254. Flex ring 226 is maintained or fixed within indentation 298 formed in rear surface 296 of front plate 254 so that extensions 268 are seated in notches 299. When inclined surface 246 of ridge 244 of syringe 204 engages chamfers 282 on flex ring 226, ridge 244 forces flex ring 226 from its relaxed state to its extended (or tensioned) state.

After ridges 244 clear the rear edge of flex ring 226 and radially outward extending tabs 250 are rotated out of contact with flex ring 226, the elastic nature of flex ring 226 causes flex ring 226 to resume its relaxed state. When flex ring 226 can resume its relaxed state, shoulder 248 of ridge 244 engages the rear edge of flex ring 226. The syringe 204 is thereby held in place by flex ring 226 and cannot be axially removed from syringe interface 202. When flex ring 226 resumes its relaxed state, an audible and/or other signal as described above can be provided to indicate to the operator that the syringe 204 has been installed on the injector. The audible and/or other signal can, for example, be created mechanically or electronically.

The flex ring 226 has attached thereto on at least one of generally flat portions 262 (corresponding generally with the long or major axis of flex ring 226) a magnet 227 or other element that cooperates with a proximity sensor 259 (e.g., a Hall effect sensor) to determine if flex ring 226 has returned to its relaxed state, for example, after insertion of syringe 204. In that regard, when flex ring 226 is in its relaxed state, magnet 227 is adjacent to the proximity sensor 259 such that the proximity sensor 259 detects a portion of the magnetic field of the magnet 227 (e.g., one of the poles of the magnetic field). Based on a position of the magnetic field relative to the proximity sensor 259 or, more particularly, a strength of the magnetic field experienced by the proximity sensor 259, the circuit may be in one of two different states. A first state may be associated with the syringe being present, and a second state may be associated with the syringe being absent.

When the flex ring 226 is in its extended state, the magnet 227 is moved away from proximity sensor 259. For example, the magnet 227 may be pulled from about 0.050" to 0.250" away from the proximity sensor 259, thereby reducing the strength of the magnetic field. This may cause the circuit of the sensor to indicate the syringe is present. For example, an output voltage may increase when the syringe is present.

The proximity sensor 259 is in operative connection with the injector head 102 to prevent operation of injector head 102 if the flex ring is in its extended state (indicating that syringe 204 is not properly or fully connected to interface or syringe interface 202). The proximity sensor 259 can also trigger an audible and/or other indication that syringe 204 is properly connected to syringe interface 202 or that syringe 204 is disengaged from syringe interface 202.

After proper connection of syringe 204 to syringe interface 202, removal of syringe from syringe interface 202 requires that syringe 204 be rotated approximately ¼ turn or approximately 90°. In general, the tabs 250 extend radially outward at least to the same extent as ridge or flange 244. When syringe 204 is rotated about its axis to a locked position, tabs 250 abut flex ring 226 and force flex ring 226 into its extended position. In this position, syringe 204 can be moved axially forward relative to syringe interface 202 so that ridge 244 passes forward of flex ring 226 and syringe 204 is released from connection to syringe interface 202.

Once syringe 204 is fully rearwardly seated within syringe interface 202, the operator must ensure that syringe 204 is rotated about its axis so that tabs 250 move out of contact with flex ring 226 and flex ring 226 is permitted to return to its relaxed state.

In some embodiments, when a syringe is inserted, the syringe operably engages a circular nylon ring with teeth to rotate. A track on the circular ring causes the elongated flex ring to expand and move the permanent magnet further away from the Hall Effect Sensor when the circular ring is rotated in one direction. By rotating the circular ring to specific positions, the distance between the magnet and the Hall Effect sensor can repeatably be selected, thereby repeatedly changing the effect of the magnetic field on the sensor.

As described below, embodiments may optionally avoid engaging the flex ring altogether and, as such, may not activate the Hall Effect sensor. However, embodiments may use a secondary mechanism (e.g., magnetic switch) for activating the sensor.

Figure 7:
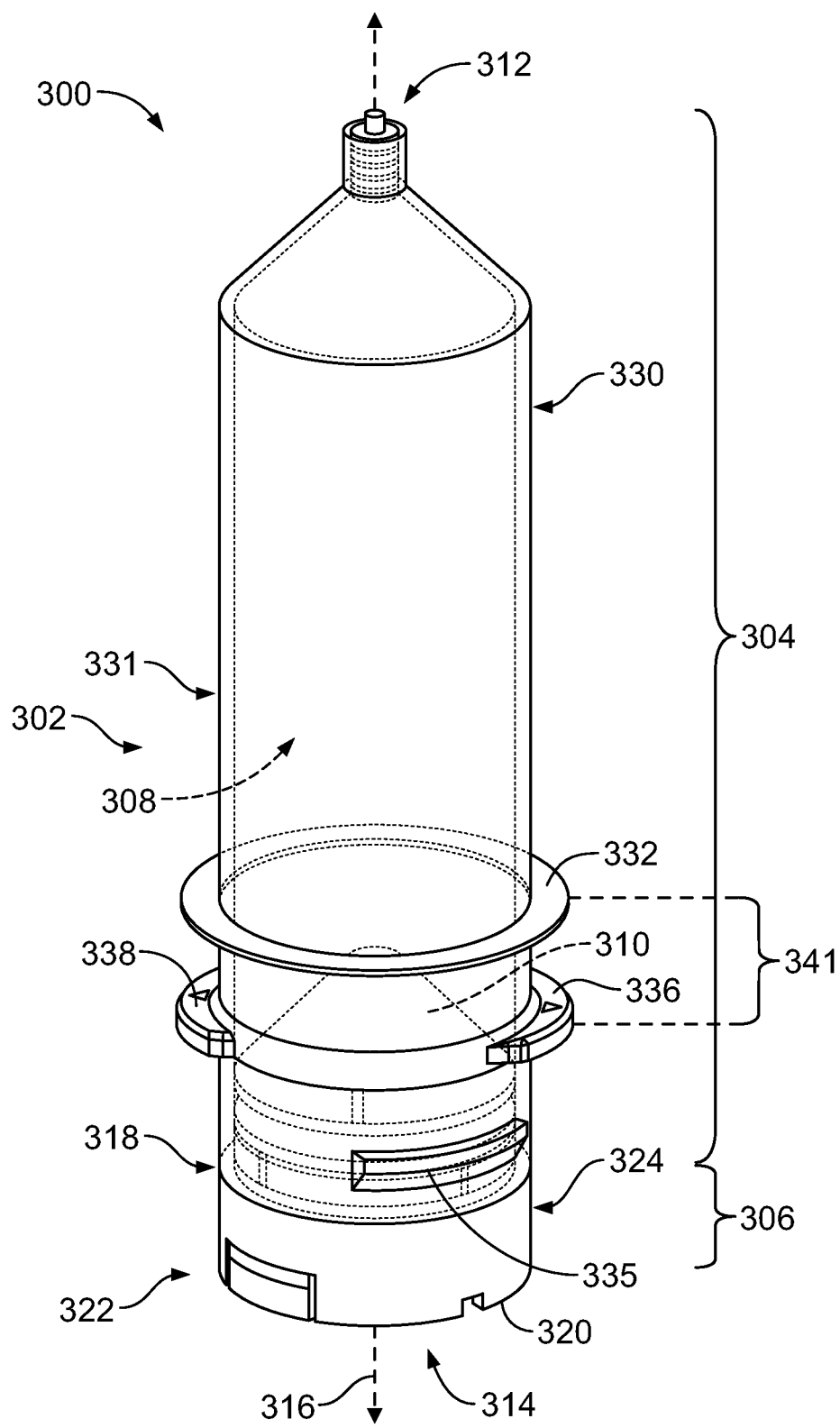
FIG. 7 is a perspective view of a syringe barrel formed in accordance with an embodiment that may be used with the known injection system of FIG. 1 and that includes a main body and a syringe base.

FIG. 7 is a perspective view of a syringe barrel 300 formed in accordance with an embodiment. The syringe barrel 125 (FIG. 2) may be similar or identical to the syringe barrel 300. The syringe barrel 300 is configured to be operably coupled to an injection system, such as the injection system 100. The syringe barrel 300 may be a multi-piece component. For example, the syringe barrel 300 includes a main portion 304 and a base portion 306 that attach to each other to form a barrel body 302 that defines a passage 308. Optionally, the syringe barrel 300 also includes a plunger 310 that is disposed within the passage 308.

The barrel body 302 extends between a tip opening 312 and a load opening 314. The passage 308 extends along a longitudinal axis 316 between the tip opening 312 and the load opening 314. The passage 308 is configured to permit the plunger 310 to advance therethrough for driving liquid through the tip opening 312.

The base portion 306 and the main portion 304 are rotatable coupled to one another at a seam 318. For example, the base portion 306 and the main portion 304 may form an interference fit and/or be threadably engaged to each other at the seam 318. In some embodiments, the plunger 310 overlaps the seam 318 at a starting position (e.g., prior to injection). The base portion has a load edge 320 that defines the load opening 314. As described herein, the base portion 306 includes an identification area 322 along a body surface 324 of the base portion 306. As shown, the body surface 324 is an external surface that faces radially away from the longitudinal axis 316. The identification area 322 is configured to identify the presence of the syringe barrel and, optionally, information regarding the syringe barrel.

The base portion 306 also has a body surface 325 (FIG. 8) that is an interior surface. Alternatively or in addition to the body surface 324 having the identification area 322, the body surface 325 may have an identification area. As such, the identification area(s) may be positioned along an interior surface of the barrel body, an exterior surface of the barrel body, or on both the interior and exterior surfaces.

The main portion 304 has an exterior surface 330. In the illustrated embodiment, the body surface 324 and the exterior surface 330 combine to form an exterior surface 331 of the barrel body 302. The main portion 304 may be at least partially translucent so that a user may determine a level of liquid within the passage 308 or an axial position of the plunger 310 within the passage 308. The base portion 306 may comprise a different material, such as a material that is more opaque than the material forming the main portion 304. Optionally, the main portion 304 may include a leading flange 332 that projects radially away from the body surface 324. The leading flange 332 extends entirely around the longitudinal axis 316. Optionally, the leading flange 332 may extend only partially around the longitudinal axis 316. The leading flange 332 may have multiple separate sections that each project radially away from the exterior surface 330 at a common axial location but different radial positions.

The main portion 304 may also include retaining shoulders 336, 338. In the illustrated embodiment, the retaining shoulders 336, 338 project from the exterior surface 330 in opposite directions away from each other and the longitudinal axis 316. The retaining shoulders 336, 338 are spaced apart from the leading flange 332 by an axial distance 341. In FIG. 7, the main portion 304 includes a pair of retaining shoulders. In other embodiments, the main portion 304 may have more than two retaining shoulders or only one retaining shoulder. As described here, the retaining shoulders may engage the fascia 104 (FIG. 1) to provide a tactile indication to the user.

Figure 8:
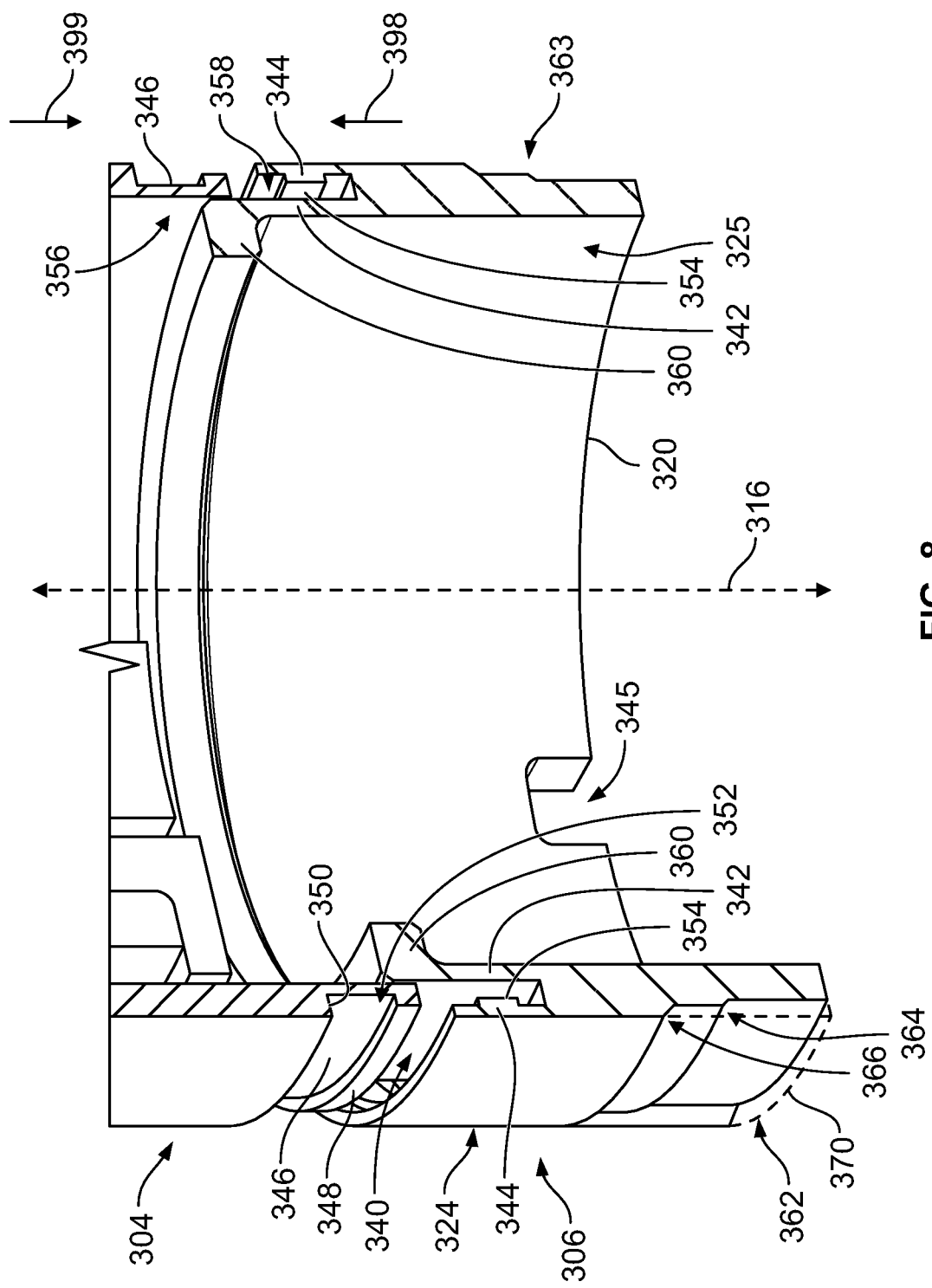
FIG. 8 is an enlarged side perspective view of a portion of the syringe barrel of FIG. 7 prior to assembly.

FIG. 8 is an enlarged sectional view of the main portion 304 and the base portion 306 prior to the base portion 306 and the main portion 304 being threadably engaged to each other. The main portion 304 and the base portion 306 are discrete elements that are rotatably coupled to each other. In other words, the main portion 304 and the base portion 306 are separate elements that combine together to form a unitary structure, the barrel body 302. The seam 318 (FIG. 7) may sufficiently impede fluid leakage during operation.

As shown, the base portion 306 includes an edge channel 340 that extends circumferentially around the longitudinal axis 316 and opens in a direction 398 along the longitudinal axis 316. The edge channel 340 is defined between an inner wall 342 and an outer wall 344. The main portion 304 has an edge track 346 that extends circumferentially around the longitudinal axis 316. The edge track 346 extends lengthwise along the longitudinal axis 316 in a direction 398 that is opposite the direction 399. The edge track 346 is sized and shaped to be received within the edge channel 340 when the main portion 304 and the base portion 306 are rotatably coupled. When engaged, the edge track 346 is held between the inner wall 342 and the outer wall 344 that define the edge channel 340.

The edge track 346 includes a rim 348, a shoulder surface 350 and a runway 352 that is defined between the shoulder surface 350 and the rim 348. The runway 352 is configured to receive a thread 354 of the base portion 306. Also shown, the edge track 346 has an inward-facing surface 356 and the inner wall 342 has an outward-facing surface 358. The inward-facing surface 356 and the outward-facing surface 358 are tapered in a similar manner with respect to the longitudinal axis 316. More specifically, as the inward-facing surface 356 and the outward-facing surface 358 extend in the direction 398 from the load opening 314 to the tip opening 312, the inward-facing surface 356 and the outward-facing surface 358 extend partially toward the tip opening 312. Due to the tapered inward-facing surface 356 and outward-facing surface 358, the base portion 306 is more readily received by the main portion 304 during engagement. More specifically, the tapered inward-facing surface 356 and outward-facing surface 358 permit more misalignment during engagement.

Also shown, the base portion 306 includes an inner ring structure 360 that is coupled to the inner wall 342 and extends circumferentially around the longitudinal axis 316. The inner ring structure 360 projects radially-inward from the inner wall 342 toward the longitudinal axis 316. The inner ring structure 360 projects radially-inward from a top of the inner wall 342 (or a distal end of the inner wall 342). The inner ring structure 360 may enhance the structural integrity of the inner wall 342 making the inner wall 342 more resistant to pressure changes within the passage 308. The tapered inward-facing surface 356 and outward-facing surface 358 may also render the barrel body 302 more resistant to pressure changes such that liquid is less likely to leak through the seam 318.

Although the above description was with reference to the base portion 306 having the edge channel 340 and the main portion 304 having the edge track 346, it should be understood that the base portion may include an edge rail and the main portion may include an edge channel in other embodiments.

The identification area 322 of the base portion 306 includes a light-propagating space 362. In the illustrated embodiment, the light-propagating space 362 is a void or recess that is shaped by the body surface 324 of the base portion 306. A dashed line 370 represents an envelope that matches the shape of base portion 306. The dashed line 370 indicates where material from the base portion 306 would be if not for the light-propagating space 362.

In some embodiments, the light-propagating space 362 is positioned along an arcuate section of the base portion 306. For such embodiments, the light-propagating space does not extend entirely around the base portion 306. The arcuate section may correspond to, for example, less than one-third of the body surface 324 within a cross-section of the base portion 306 that is taken perpendicular to the longitudinal axis. In the illustrated embodiment, the arcuate section corresponds to less than one-quarter of the body surface 324 within the cross-section of the base portion 306 or less than one-fifth of the body surface 324 within the cross-section of the base portion 306.

The light-propagating space 362 begins at the load edge 320 and extends to reflective ramps 364, 366 of the body surface 324. The reflective ramps 364, 366 project away from the longitudinal axis 316 at a non-orthogonal angle and define an end of the light-propagating space 362. The angle may be about 45° although other angles may be used. The reflective ramps 364, 366 have predetermined sizes and positions relative to each other in order to reflect a predetermined set of light signals radially away from the barrel body 302. The predetermined set of light signals may constitute a code for confirming the presence of the syringe barrel 300 within the receiving cavity (not shown) of the injector head (not shown). The code may also provide information relating to the syringe barrel 300 or the contents of the syringe barrel 300, such as the liquid within the syringe barrel, a volume of the liquid, the supplier of the liquid, or the date on which the liquid was provided to the syringe barrel.

Also shown, the base portion 306 includes a notch 345 that opens at the load edge 320. The notch 345 may provide a reference feature by which the syringe barrel 300 may be oriented. More specifically, the notch 345 may engage a corresponding feature of the injector head so that the syringe barrel 300 has a proper orientation with respect to the injector head.

Figure 9:
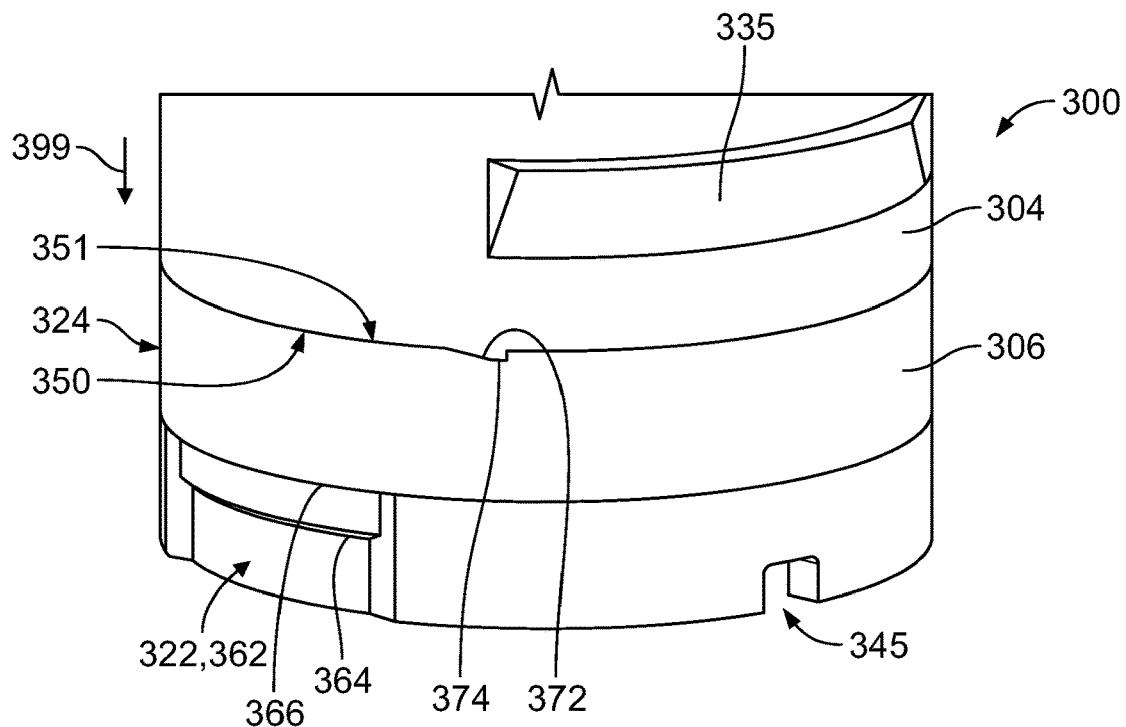
FIG. 9 is a side view of the syringe barrel after assembly and in a fully-engaged condition.

FIG. 9 is a side view of a portion of the syringe barrel 300 after the main portion 304 and the base portion 306 have been threadably engaged and are in a fully engaged position. In some embodiments, at least one of the main portion 304 or the base portion 306 includes a boss that is configured to be received within a recess of the other portion. For example, in the illustrated embodiment, the main portion 304 includes a boss 372 (e.g., tooth) that projects in the direction 399 away from the shoulder surface 350. The base portion 306 includes a recess 374 that is sized and shaped to receive the boss 372. The boss 372 and the recess 374 are located such that the syringe barrel 300 achieves the fully engaged position as the boss 372 is received within the recess 374. As the main portion 304 and the base portion 306 are threadably engaged, the boss 372 may engage a top surface 351 of the outer wall 344 as the boss 372 approaches the recess 374. When the boss 372 engages the top surface 351 of the outer wall 344, the friction generated may be felt by the user who is threadably engaging the main portion 304 and the base portion 306. The noticeable increase in friction may be immediately followed by a decrease in friction as the boss 372 enters into the recess 374. Moreover, the boss 372 and the recess 374 may be shaped such that further rotation is prevented.

Also shown, the main portion 304 includes a shoulder 335 that projects radially away from the exterior surface 330. The shoulder 335 is configured to be positioned behind the flex ring of the injector head. The shoulder 335 may prevent the syringe barrel 300 from being inadvertently removed from the receiving cavity during operation. As shown, the shoulder 335 extends only partially around a circumference of the exterior surface 330. Although only one shoulder 335 is shown, embodiments may include more than one shoulder 335. For example, embodiments may include two shoulders 335 that are located 180° apart from one another.

In the fully engaged position as shown in FIG. 9, one or more physical features of the main portion 304 have predetermined positions relative to the positions of one or more physical features of the base portion 306 and vice-versa. For example, the shoulders 335 may have a predetermined position when the syringe barrel 300 is operably engaged to the injector head. As another example, the identification area 322 of the body surface 324 may have a predetermined position when the syringe barrel 300 is operably engaged to the injector head. In this predetermined position, a light source may illuminate the reflective ramps 364, 366 at an end of the light-propagating space 362. Because the reflective ramps 364, 366 are at a predetermined position the light signals reflected by the reflective ramps 364, 366 are directed to a light detector that is located at a predetermined fixed position.

In some embodiments, the syringe barrel 300 may include at least two identification areas 322 or two light-propagating spaces 362, 363 (shown in FIG. 8) along the body surface 324. The light-propagating spaces 362, 363 may be on opposite sides of the barrel body. For example, the two light-propagating spaces 362, 363 may be 180° apart. In some embodiments, the shoulders 335, the light-propagating spaces 362, 363, and the retaining shoulders 336, 338 allow the syringe barrel 300 to be oriented in only two possible rotational orientations when inserted into the receiving cavity. As described below, the fascia may be shaped to receive the syringe barrel in only two possible orientations that are 180° apart.

In the illustrated embodiment, the light-propagating space 362 is shaped by the body surface 324, which is an exterior surface that faces radially away from the longitudinal axis 316. Alternatively or in addition to the body surface 324, the body surface 325 may be shaped to define a light-propagating space (not shown), which may be similar to one or more of the light-propagating spaces described herein. For example, the body surface 325 could include angled surfaces that reflect and/or refract the light signals away from the barrel body. For example, in such embodiments, the base portion may have an opening therethrough that permits the reflected light signals to propagate from an interior of the base portion to an exterior of the base portion. Alternatively, the light signals may be incident upon the interior surface and be refracted through the base portion to the exterior of the base portion. Accordingly, the syringe barrel 300 may have one or more surfaces along an exterior of the barrel body 302, one or more surfaces along an interior of the barrel body 302, or surfaces along both the exterior and interior that are configured to reflect and/or refract the light signals away from the barrel body 302. In such embodiments, the light signals may propagate in free space along the barrel body 302 until being incident upon the surfaces of the barrel body 302.

Figure 10:
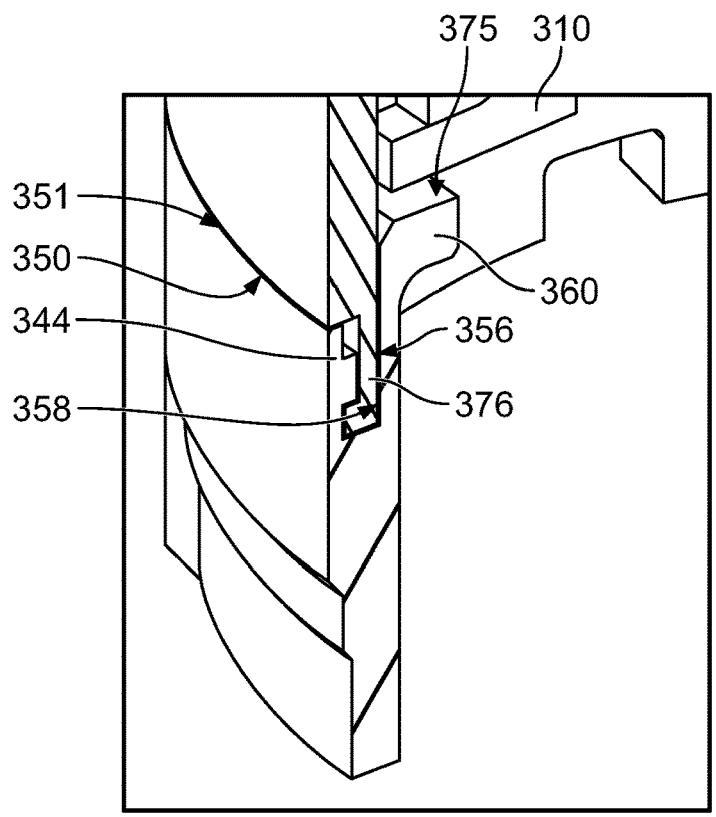
FIG. 10 is a side sectional view of the syringe barrel after assembly and in a fully-engaged condition illustrating locking features of the syringe barrel.

FIG. 10 is a sectional view of a portion of the syringe barrel 300 when the main portion 304 and the base portion 306 are in a fully-engaged condition. As shown, the seam 318 is defined by the shoulder surface 350 and the top surface 351 of the outer wall 344. The inward-facing surface 356 and the outward-facing surface 358 engage each other along and angled interface 376. Optionally, the inner ring structure 360 may provide a seating area 375 for the plunger 310. The inner ring structure 360 also increases the rigidity of the inner wall 342 such that the inner wall 342 is resilient to flexing when a sharp pressure change occurs within the passage 308. Because of the angled interface 376, the seam 318, and the inner ring structure 360, the multi-piece syringe barrel 300 may be resistant to leakage.

Figure 11:
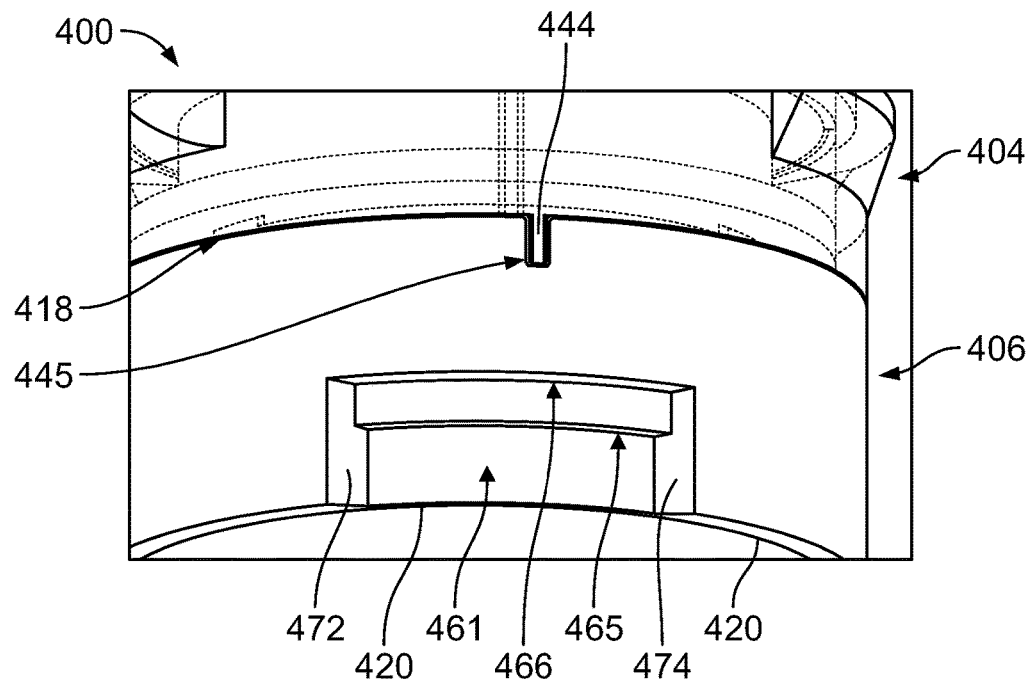
FIG. 11 is a side perspective view of a portion of a syringe barrel formed in accordance with an embodiment.

FIG. 11 is a bottom perspective view of a portion of a syringe barrel 400. The syringe barrel 400 may be similar to the syringe barrel 300 (FIG. 7) and include a main portion 404 and a base portion 406. As shown, the main portion 404 and the base portion 406 are engaged to each other along a seam 418. The main portion 404 includes a finger 444, and the base portion 406 includes a slot 445.

Also shown in FIG. 11, a light-propagating space 461 is defined between opposite side surfaces 472 and 474. For such embodiments in which the light-propagating space is a void in the body surface of the syringe barrel, the light-propagating space may be referred to as a light-propagating recess. Similar to the light-propagating space 362, the light-propagating space 461 extends from a load edge 420 to reflective ramps 465 and 466.

Figure 12:
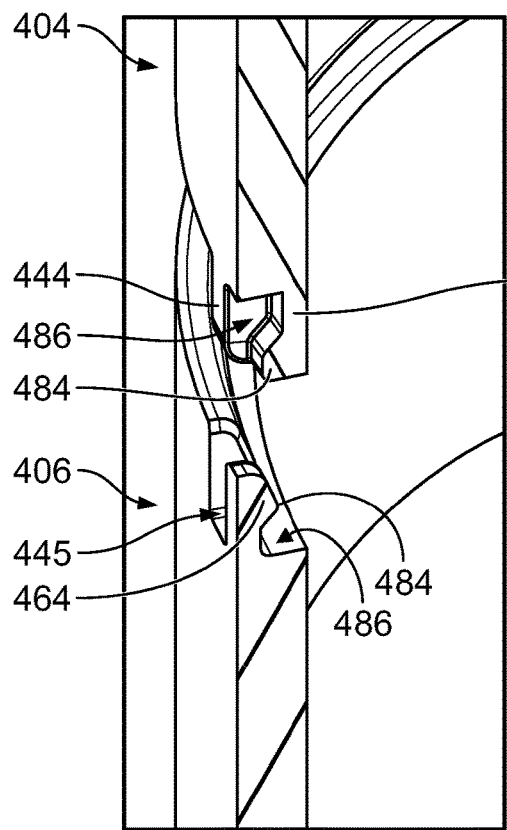
FIG. 12 is a side cross-sectional view of the syringe barrel of FIG. 11 prior to assembly illustrating features in greater detail.
Figure 13:
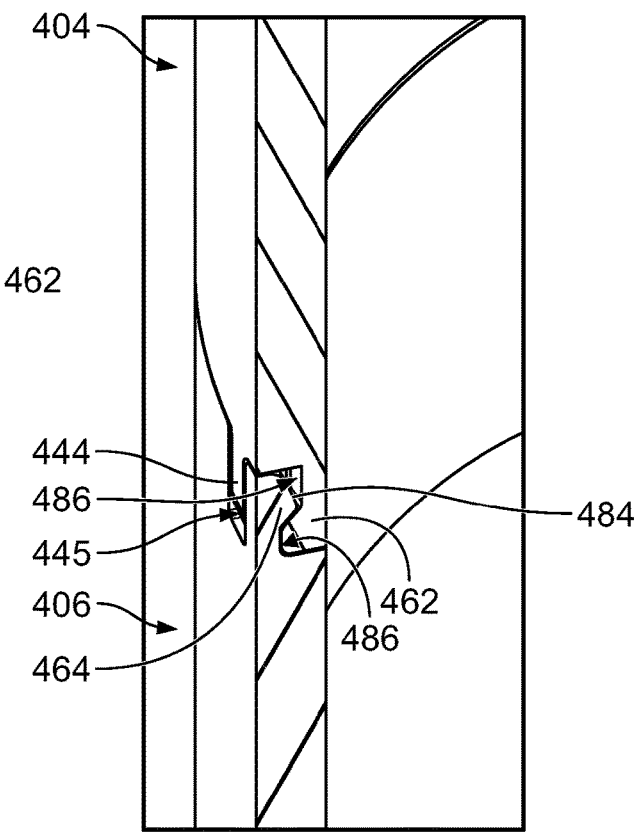
FIG. 13 is a side cross-sectional view of the syringe barrel of FIG. 11 after assembly and in a fully-engaged condition.

FIG. 12 and FIG. 13 are sectional views of the syringe barrel 400 prior to and after coupling, respectively, the main portion 404 and the base portion 406. In the illustrated embodiment, the main portion 404 and the base portion 406 may be snap fit such that the two pieces may be aligned along the longitudinal axis (not shown) and pressed toward each other with an axial force. An inner wall 462 of the main portion 404 and an outer wall 464 of the base portion 404 each have a ridge 484 and a channel 486 defined by the ridge 484. As the axial force is applied, the inner and outer walls 462, 464 may be deflected, thereby allowing the ridges of the inner and outer walls 462, 464 to clear each other and snap into the corresponding channels. In the illustrated embodiment, the main portion 404 and the base portion 406 can only be snap-fit if the finger 444 is aligned with the slot 445.

In other embodiments, the main portion 404 and the base portion 406 may be rotatably coupled. The finger 444 may be a flexible finger that is capable of deflecting radially-inward towards the longitudinal axis. As the main portion 404 and the base portion 406 are rotatably coupled, the finger 444 may be deflected inward. When the finger clears the slot 445, the finger 444 may flex into the slot 445, thereby preventing further rotation of the main portion 404 and the base portion 406.

Figure 14:
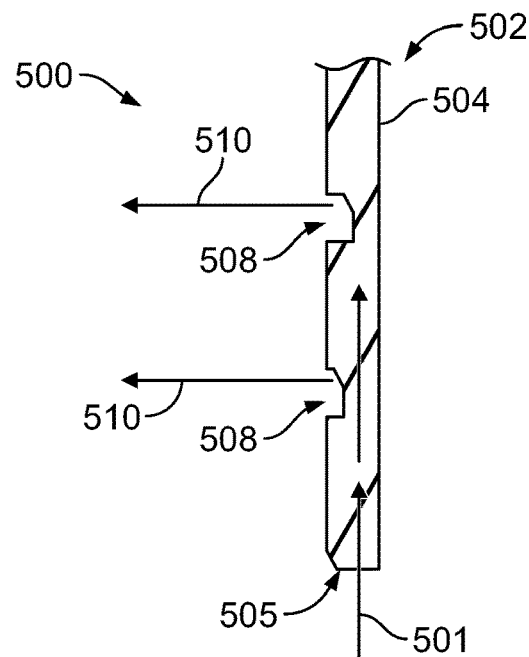
FIG. 14 is a cross-sectional view of a portion of a known syringe illustrating refraction of light from the syringe.

FIG. 14 is a schematic view of an identification area 500 used by a known system. In the known system, a light source generates light 501 that propagates through a wall 504 of the syringe 502. For example, a laser or LED light source can provide light 501 through an edge surface 505 of the wall 504. The light 501 may propagate through the wall 504 and interact with discontinuities in the material of the wall 504, thereby causing refraction in which light exits the syringe 502 in a predetermined manner and is directed away from the syringe 502. More specifically, the wall 504 may include open-side grooves or channels 508 having surfaces with predetermined angles so that the light may interact with the wall 504 and generate light signals 510 that propagate away from the syringe 502.

Figure 15A:
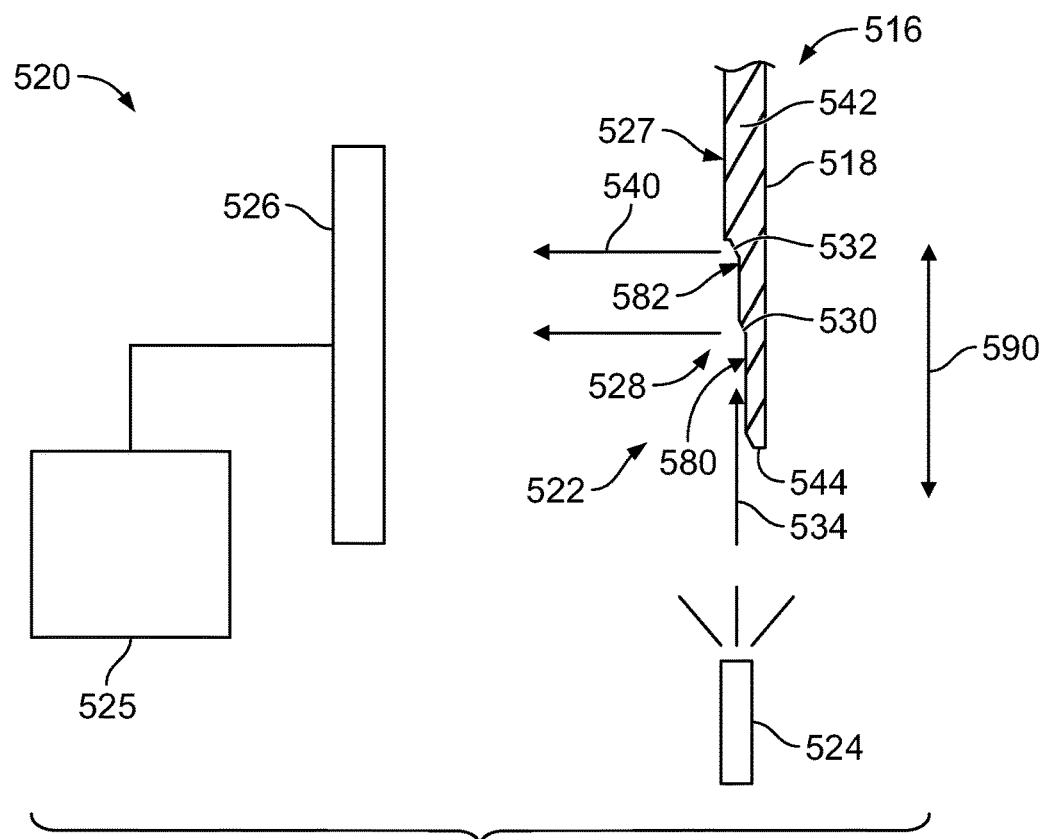
FIG. 15A is a cross-sectional view of a portion of a syringe barrel formed in accordance with an embodiment illustrating reflection of light from an exterior surface of the syringe barrel.

FIG. 15A illustrates a syringe-confirmation assembly 520 that may be used by one or more embodiments described herein. For example, the syringe-confirmation assembly 520 may include an identification area 522 of a syringe barrel 516, a light source 524, a light detector 526, and a controller 525. The identification area 522 is a shaped portion of the syringe barrel 516 having a base wall 518 of a base portion 542. In some embodiments, the syringe-confirmation assembly 520 includes the syringe barrel 516 and the light source 524 and/or the light detector 526. The base wall 518 has an exterior body surface 527 that is shaped to provide a light-propagating space 528. The light-propagating space 528 may be similar or identical to the light-propagating spaces 362 (FIG. 8) and 462 (FIG. 11).

The light-propagating space 528 ends at reflective ramps 530 and 532. As shown, the light source 524 generates light 534 that propagates alongside the base wall 518 within the light-propagating space 528. The light 534 is reflected by the reflective ramps 530, 532 in a predetermined manner. More specifically, the reflective ramps 530, 532 are sized, shaped, and positioned so that light signals 540 are directed radially away from the base wall 518 and towards a predetermined location.

The light-propagating space 528 may have at least first and second levels 580, 582 of the exterior body surface 527. The first level 580 is closer to a longitudinal axis 590 than the second level 582. In other words, the second level 582 has a greater elevation along the exterior body surface 527. As shown in FIG. 15, the first level 580 has a greater length along the longitudinal axis 590 than a length of the second level 582. Also shown, the base portion 542 has a load edge 544 that defines a load opening. The load edge 544 has a reduced thickness.

The light source 524 may be configured to generate electromagnetic radiation that has a designated wavelength or a designated range of wavelengths. For example, the electromagnetic radiation may be optical radiation within the visible spectrum (e.g., 390 nanometers (nm) to 700 nm). The electromagnetic radiation may also be optical radiation within a generally non-visible spectrum, such as ultraviolet (10 to 400 nm) and infrared (700 nm to 1550 nm or more). It should be understood that a variety of light sources, detectors, and materials exist and that the light sources, detectors, and materials may be configured for reflecting and detecting light signals.

The light detector 526 is positioned at the predetermined location and detects the light signals 540. The light detector 526 is communicatively coupled to the controller 525 that reads the light signals 540. For example, the controller 525 may have access to a lookup table having a library of recognizable light signals. The controller 525 may identify the detected light signals with light signals stored in the lookup table to determine information about the syringe. Accordingly, and unlike the light detection system of FIG. 14, light may propagate alongside the base wall 518 without being transmitted through the base wall 518. The light may then be reflected by the base wall 518 towards the light detector 526.

Optionally, the base portion may be incapable of having an appreciable amount of electromagnetic radiation having a detectable wavelength propagate from the load edge 544 through the base wall 518 to the reflective ramps 530, 532. For example, at least one of the following may exist: (a) the base portion is shaped from an opaque material; (b) the exterior surface of the base portion is coated with an opaque material; or (c) the base portion includes discontinuities therein that scatter the electromagnetic radiation. In other words, the discontinuities scatter the electromagnetic radiation such that the electromagnetic radiation may not be reflected and sufficiently detected. As used herein, the term "opaque material" means a material in which the electromagnetic radiation is unable to propagate through such that the electromagnetic radiation may be reflected and detected.

In some embodiments, the base wall 518 is fabricated from a material that is different from material used for other portions of the syringe barrel. For instance, the main portion 304 (FIG. 7) and the main portion 404 (FIG. 11) may comprise a material that is different than the material for the base portions 304, 404. The material used for the base portions 304, 404 may be more suitable for reflecting light. By way of example, the material for the base wall 518 or the base portion may be polyethylene terephthalate (PET). Other methods of providing the base wall may include pad printing, hot stamping, insert molding, or three-dimensional printing. In particular embodiments, the exterior surface of the base wall 518 may be stamped or pressed with an opaque material or coated with an opaque material. The opaque material may include a reflective foil.

Figure 15B:
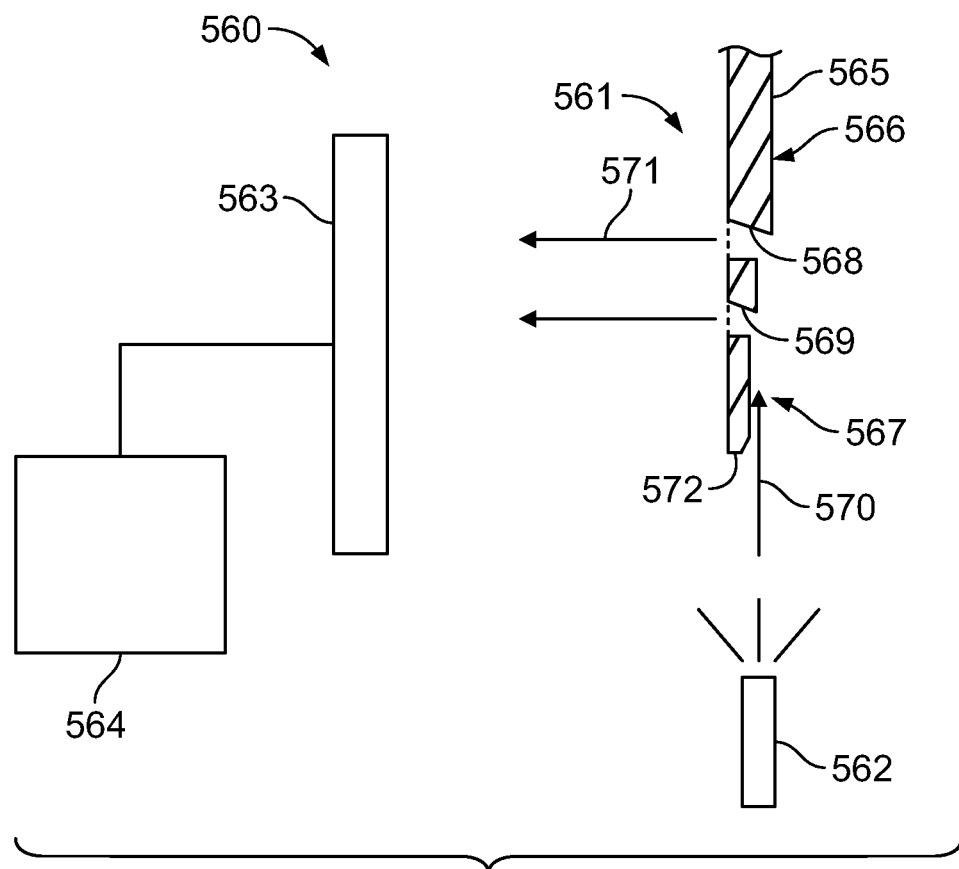
FIG. 15B is a cross-sectional view of a portion of a syringe barrel formed in accordance with an embodiment illustrating reflection of light from an interior of the syringe barrel.

FIG. 15B illustrates a syringe-confirmation assembly 560 that may be used by one or more embodiments described herein. The syringe-confirmation assembly 560 includes an identification area 561, a light source 562, a light detector 563, and a controller 564. The identification area 561 is a shaped portion of a syringe barrel having a base wall 565. The base wall 565 has an interior body surface 566 that is shaped to provide a light-propagating space 567. The light-propagating space 567 may be similar to other light-propagating spaces described herein. The light-propagating space 567 ends at reflective ramps 568 and 569. The base wall 565 also includes respective openings therethrough that are partially defined by the reflective ramps 568, 569.

As shown, the light source 562 generates light 570 that propagates alongside the base wall 565 within the light-propagating space 567. The light 570 is reflected by the reflective ramps 568, 569 in a predetermined manner. More specifically, the reflective ramps 568, 569 are sized, shaped, and positioned so that light signals 571 are directed radially away from the base wall 565 and towards a predetermined location.

Optionally, the base portion may be incapable of having an appreciable amount of electromagnetic radiation having a detectable wavelength propagate from a load edge 572 through the base wall 565 to the reflective ramps 568, 569. For example, at least one of the following may exist: (a) the base portion is shaped from an opaque material; (b) the interior surface of the base portion is coated with an opaque material; or (c) the base portion includes discontinuities therein that scatter the electromagnetic radiation.

Figure 16:
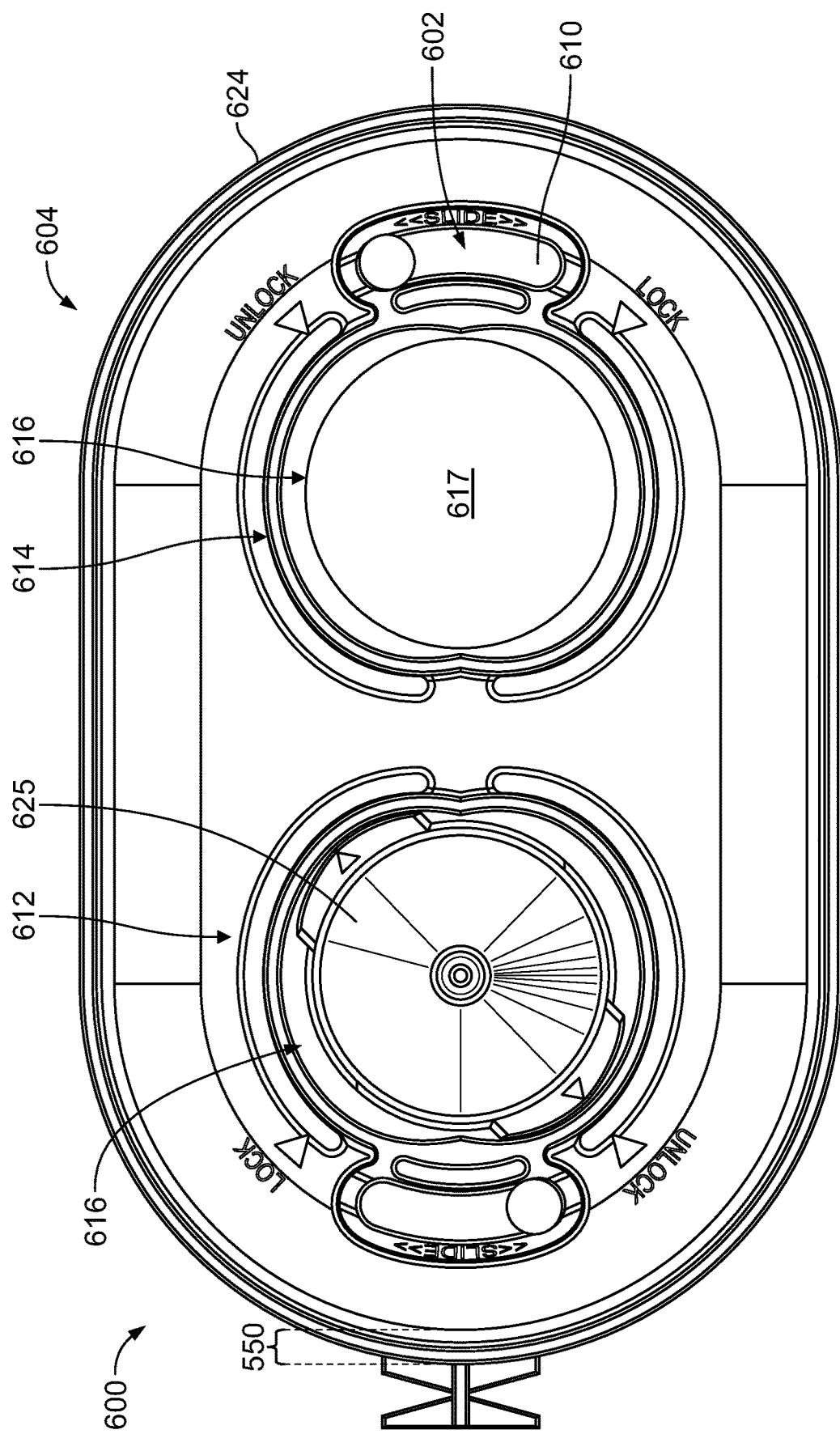
FIG. 16 is an end view of a portion of an injection system in accordance with an embodiment when the syringe barrel is in releasable position.
Figure 17:
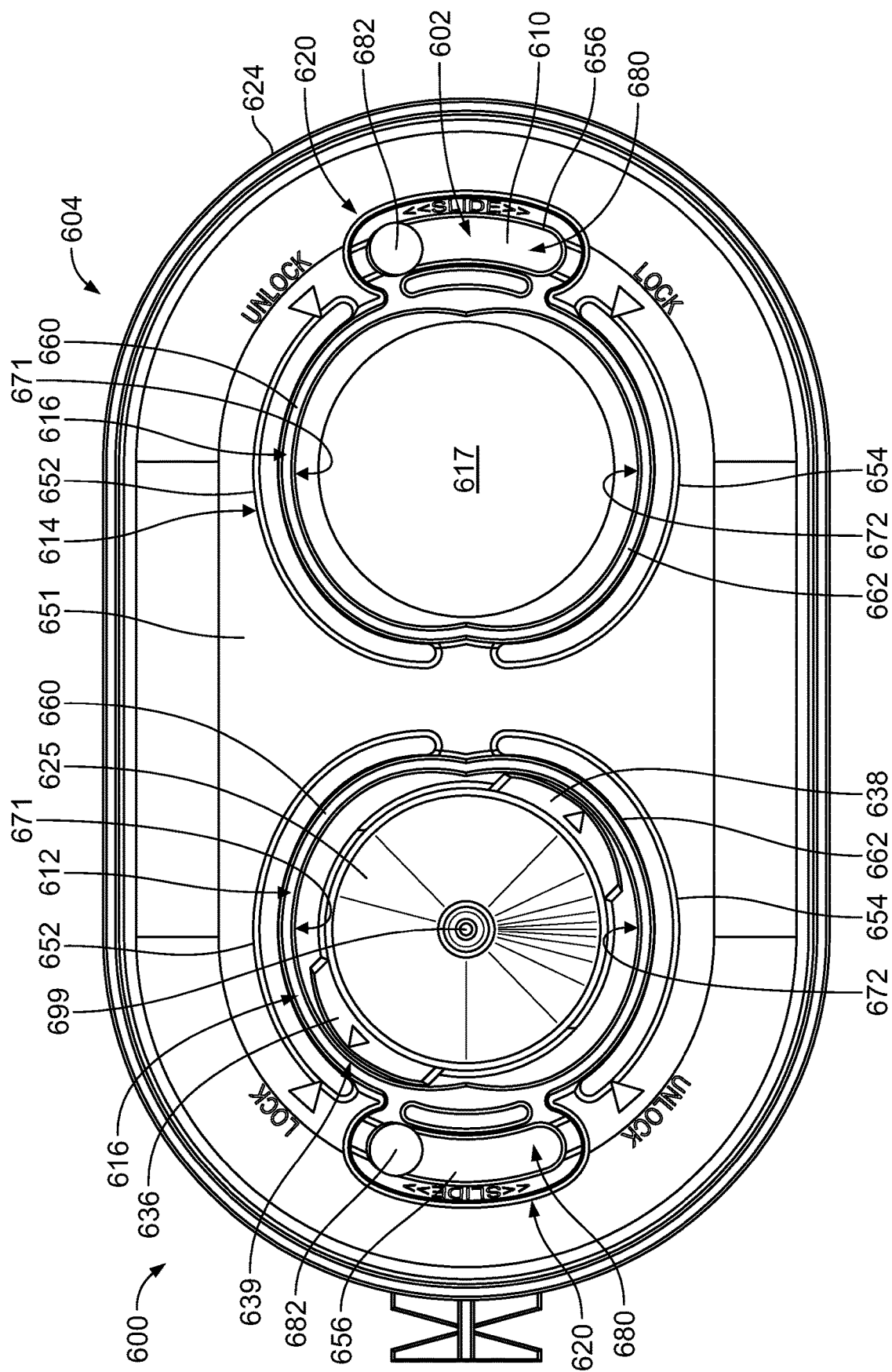
FIG. 17 is an end view of a portion of the injection system of FIG. 16 when the syringe barrel is in a loaded position.

FIG. 16 and FIG. 17 are end views of an injection system 600 having a fascia 604. The injection system 600 and the fascia 604 may be similar to the injection system 100 and the fascia 104, respectively, of FIG. 1. As shown in FIGS. 16 and 17, the fascia 604 is positioned on an active side 610 of an injector head 602. A peripheral lip 624 extends along a perimeter of the fascia 604. The fascia 604 is positioned such that syringe openings 616 are aligned with respective cavities 617 of the injector head 602. When aligned the syringe openings 616 and the receiving cavities 617 form respective ports 612, 614 that are configured to receive a syringe barrel 625 therethrough. In FIG. 16, the syringe barrel 625 is mated with the port 612 and in an unlocked position, which may also be referred to as a start position or a releasable position. In FIG. 17, the syringe barrel 625 is in the locked position. In the locked position, the syringe barrel 625 is operably engaged to the injector head 602 such that the injector head 602 controls the syringe barrel 625.

As shown in FIG. 17, the fascia 604 has a plurality of radially-inward surfaces 671, 672 that define a portion of the syringe opening 616. As described herein, the radially-inward surfaces and the syringe barrel 625 may be shaped relative to each other such that the radially-inward surfaces and the syringe barrel 625 slidably engage each other during an operating turn in which the syringe barrel 625 is rotated by the user to operably engage the syringe barrel 625 and the injector head 602. In the illustrated embodiment, the radially-inward surfaces 671, 672 provide a non-circular shape to the syringe opening. For example, the syringe opening 616 may be oval-shaped or have two lobes.

In particular, the radially-inward surfaces and the syringe barrel 625 may be shaped relative to each other such that a torque for rotating the syringe barrel 625 from the start position is less than a torque for rotating the syringe barrel 625 at a mid-point between the start and loaded positions. Alternatively or in addition to the above, the radially-inward surfaces and the syringe barrel 625 may be shaped relative to each other such that a torque for rotating the syringe barrel 625 from the loaded position is less than a torque for rotating the syringe barrel 625 at a mid-point between the start and loaded positions.

In the illustrated embodiment, each pair of radially-inward surfaces 671, 672 and the syringe barrel 625 are configured such that the torque for rotating the syringe barrel 625 from the start position or from the loaded position is less than the torque for rotating the syringe barrel at the mid-point between the start and load positions. In other words, a user exerting effort to rotate the syringe barrel 625 from the start position to the loaded position or from the loaded position to the start position will notice that the effort to rotate is easier at the beginning or the end of the operating turn than at a midway point of the operating turn. Accordingly, the user is provided a tactile indication that the operating turn is productive such that the syringe barrel 625 is being engaged with the injector head 602 and also given a tactile indication that the operating turn has ended because the effort to turn the syringe barrel 625 decreased immediately before stopping.

Also shown in FIG. 17, the syringe barrel 625 has retaining shoulders 636, 638. Each of the retaining shoulders 636, 638 has an outer edge 639 with a radius of curvature that is similar to a radius of curvature of the syringe barrel 625. As such, the outer edges 639 extend parallel to an exterior surface of the syringe barrel 625 as the outer edge 639 extends around a longitudinal axis 699 of the syringe barrel 625.

Figure 18:
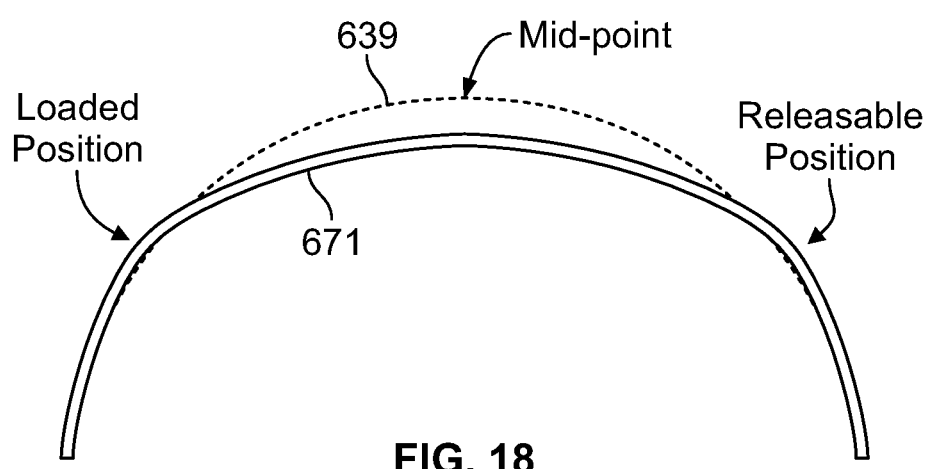
FIG. 18 is a schematic view of a mechanism to provide a tactile indication to a user.

Turning to FIG. 18, the radially-inward surface 671 is identified by a solid line. The dashed line represents a path that would be taken by the outer edge 639 of a retaining shoulder during an operating turn. As shown, the radially-inward surface is positioned inward from the dashed line. As such, the outer edge 639 engages the radially-inward surface 671 during the operating turn. However, the engagement is not significant when the outer edge 639 is in the loaded position or in the releasable position. In the illustrated embodiment, the engagement (or friction) is strongest at the mid-point. When the outer edge 639 engages the radially-inward surface 671, the radially-inward surface 671 may be partially deflected. Friction generated between the outer edge 639 and the radially-inward surface 671 drags or impedes the operating turn. More specifically, the friction requires more effort or torque in order to rotate the syringe barrel. As such, the friction is least when the outer edge 639 is near the releasable position or the loaded position and greatest when the outer edge 639 is at the mid-point. The change in effort to rotate the syringe barrel is configured to be noticeable by the user.

Returning to FIG. 17, in the illustrated embodiment, the radially-inward surfaces 671, 672 are surfaces of deflectable ribs 660, 662, respectively. More specifically, the fascia 604 has a cover body 651 that includes the syringe openings 616, tactile openings 652, 654, and switch openings (or slots)

656. The tactile openings 652, 654 and the switch openings 656 may be referred to as secondary openings. The tactile openings 652 are slots that extend parallel to but spaced apart from a perimeter of the respective syringe openings 616 such that a strip of material exists between the tactile openings 652 and the respective syringe openings 616. The strips of material are the deflectable ribs 660. Likewise, the tactile openings 654 are slots that extend parallel to but spaced apart from a perimeter of the respective syringe openings 616 such that a strip of material exists between the tactile openings 654 and the respective syringe openings 616. The strips of material are the deflectable ribs 662.

The deflectable ribs 660, 662 may also have radially-outward surfaces that define the corresponding tactile openings 652, 654. The deflectable ribs 660, 662 may move when engaged with the syringe barrel such that a size or shape of the tactile opening changes. In some embodiments, the injection system may include a shroud, such as a shroud 708 (FIG. 19), that is sized and shaped to cover the tactile openings 652, 654. The shroud 708 may also be referred to as a side cover in some embodiments.

Each pair of deflectable ribs 660, 662 may cooperate together to provide a tactile indication to the user performing an operating turn on the syringe barrel 625. In other embodiments, only a single deflectable rib may be used. In the illustrated embodiment, the radially-inward surfaces are located along deflectable ribs of the fascia. In other embodiments, however, the radially-inward surfaces may exist along other physical features that are deflectable or compressive.

Also shown in FIG. 17, magnetic switches 620 each include a channel 680 extending alongside the syringe opening 616 and a permanent magnet 682. In other embodiments, the magnetic switches 620 may include an electromagnet. The magnetic switch 620 and the permanent magnet 682 are positioned outside of the injector head in the illustrated embodiment. For example, the permanent magnet 682 (or the electromagnet) may be immediately adjacent to the injector head such that the permanent magnet 682 engages the injector head or has only a nominal gap therebetween (e.g., less than 5 millimeters). The permanent magnet 682 may be snap-fit from an underside of the fascia 604. The permanent magnet 682 is permitted to slide along or through the channel 680 and along the active site 610. The permanent magnet 682 may be configured to move between different positions. For example, the permanent magnet 682 may be moved to a first position to trigger the sensor. The permanent magnet 682 may be moved to a second position to trigger the sensor.

Figure 4:
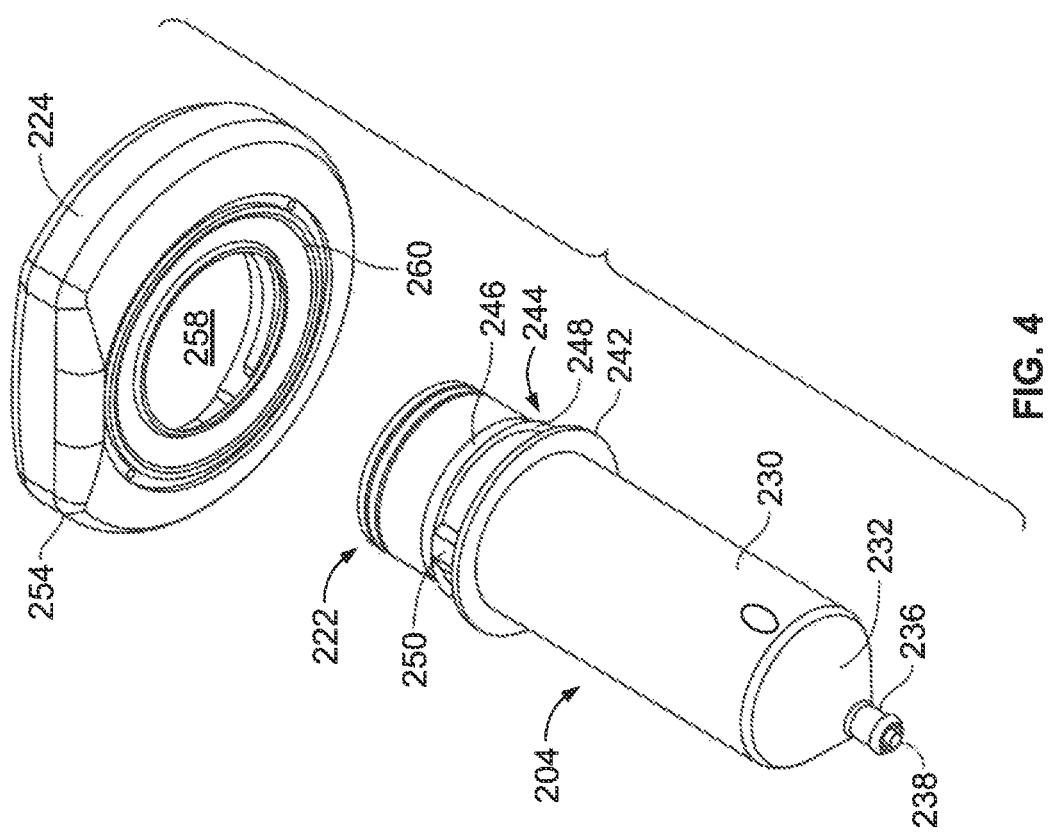
FIG. 4 is a perspective view of the syringe of the known injector sub-assembly of FIG. 3 that is poised to be seated within the syringe interface.
Figure 3:
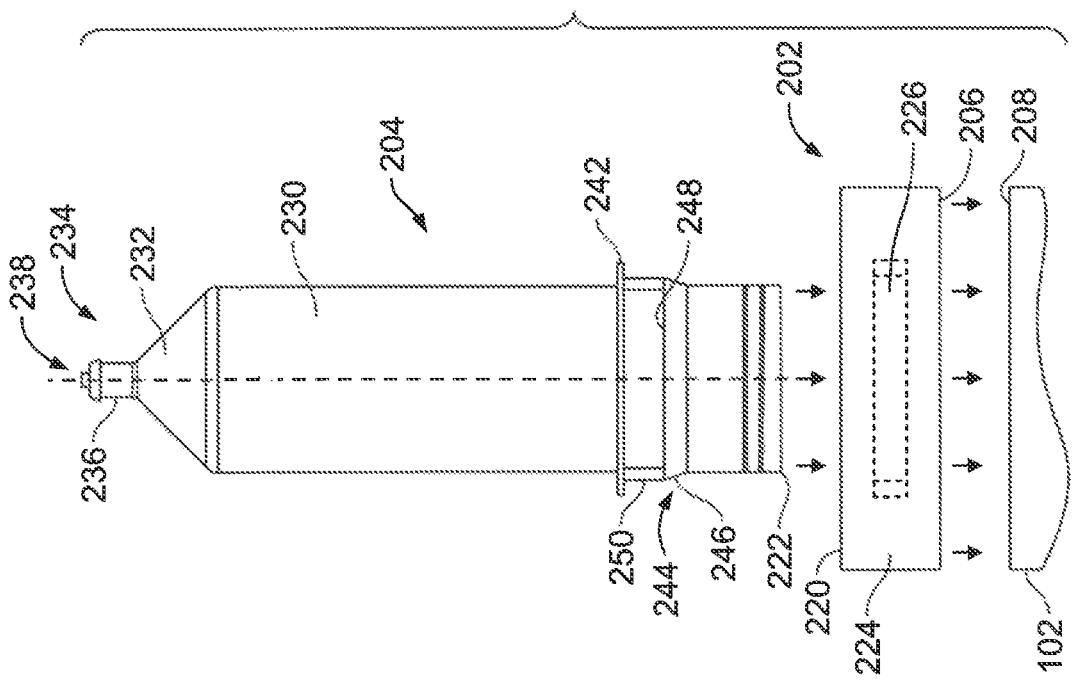
FIG. 3 is a side view of a known injector sub-assembly that includes a syringe interface and a syringe.
Figure 5:
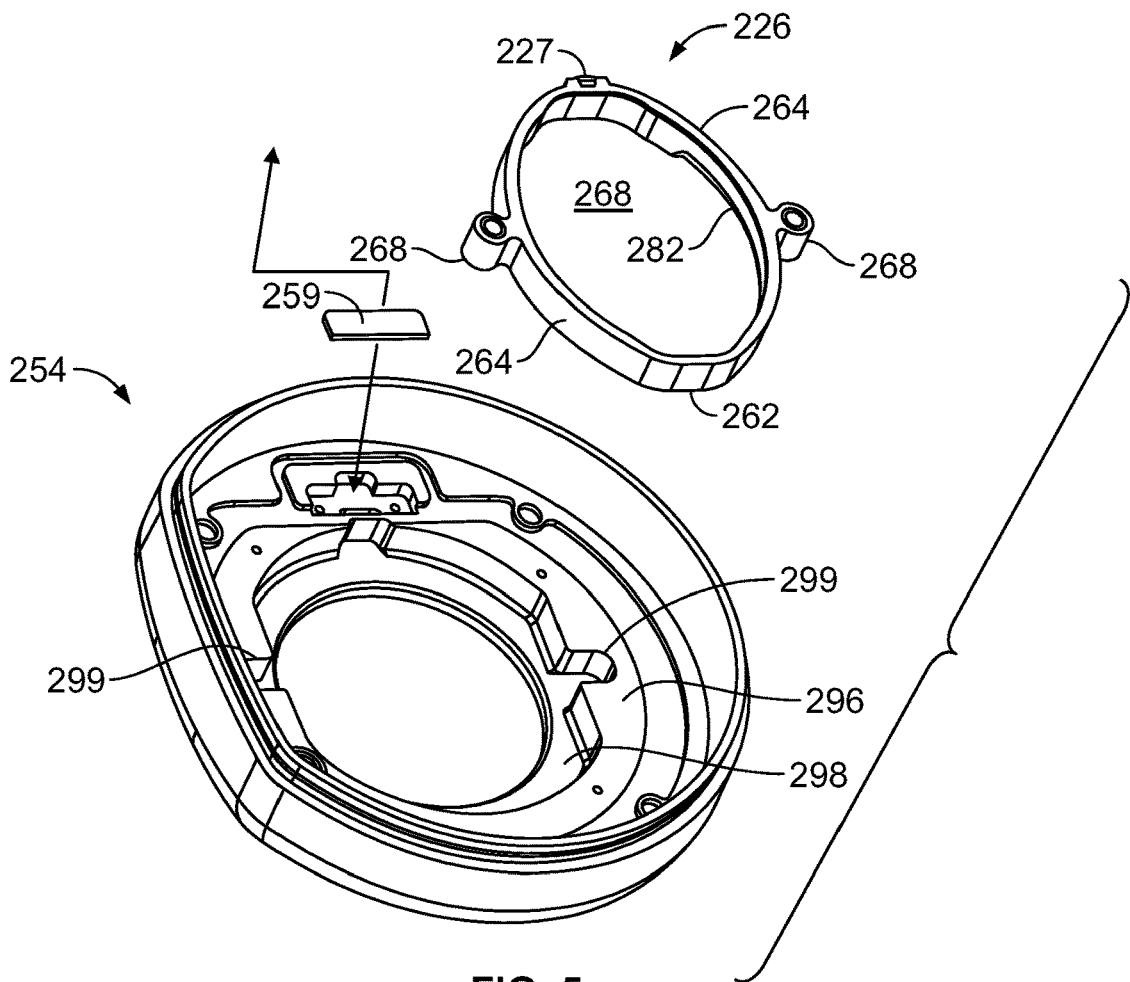
FIG. 5 is a rear perspective view of the syringe interface of FIG. 3 with a flex ring disconnected from a connector housing of the syringe interface.
Figure 6:
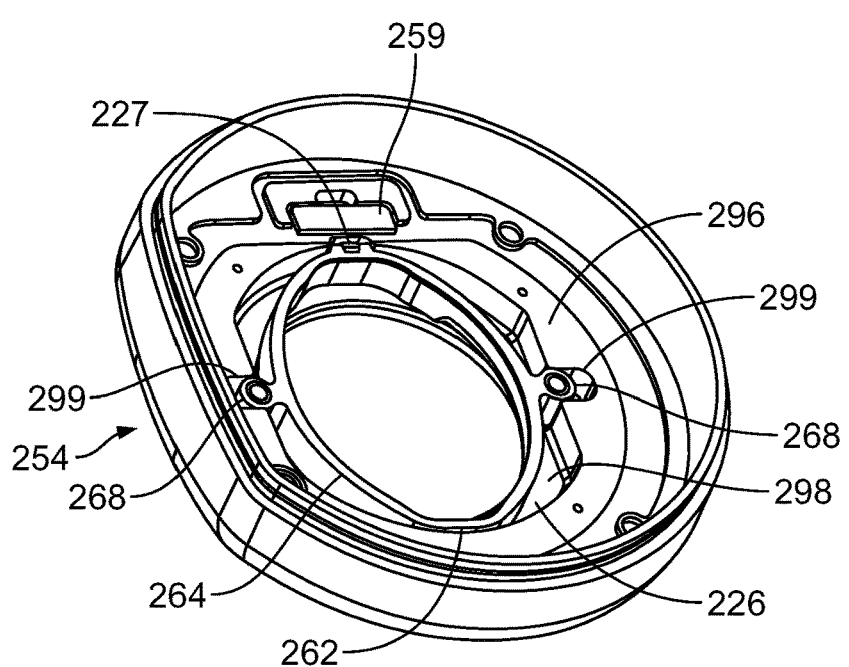
FIG. 6 is a rear perspective view of the syringe interface of FIG. 3 with the flex ring installed within the connector housing.

As described above with respect to FIGS. 3-6, the active side 610 may be adjacent to a sensor of the injector head 602. For example, a straight line that is less than or equal to five (5) centimeters (cm) may extend from a point of the active side 610 to the internal sensor. In certain embodiments, the straight line is less than three (3) cm or less than two (2) cm. The permanent magnet 682 generates a magnetic field. As the magnetic field moves with the permanent magnet and crosses the sensor in the injector head 602, the sensor is triggered in a similar manner as the proximity sensor 259 (FIG. 5). In the known system, the magnet 227 (FIG. 5) is moved with respect to the proximity sensor 259 (FIG. 5) when the flex ring 226 is engaged by the known syringe.

In embodiments of the present application, however, the magnetic switch 620 may be activated independently from the rotation of the syringe barrel 625. For example, the syringe barrel 625 may not engage or cause the flex ring 226 (FIG. 3) to move when the syringe barrel 625 operably engages or is operably engaged with the injector head 602. Consequently, the internal magnet does not move and the magnetic field of the internal magnet does not move and trigger the internal sensor, such as the sensor 229 (FIG. 5).

Nonetheless, external magnets described herein are capable of independently triggering the internal sensor. When the internal sensor is triggered by the magnetic switch 620, the injector head 602 may respond. For example, the injector head 602 may illuminate the reflective ramps to generate light signals and confirm the presence of the syringe barrel 625 or identify the syringe barrel 625. The injector head 602 may also prepare the pistons by advancing them through the passage to engage the plunger within the passage. Additionally, in some embodiments, the syringe barrel 625 may be partially retracted so that the leading flange (not shown in FIG. 17) engages the lip 260 (FIG. 4).

It is noted that some embodiments may be capable of operating with syringe barrels described herein, such as the syringe barrels 300, 625, 702, in addition to other known syringe barrels, such as the syringe 204. Accordingly, an injector head may be capable of operably engaging syringe barrels having different designs in which one design engages the flex ring and in which another design does not engage the flex ring.

Figure 19:
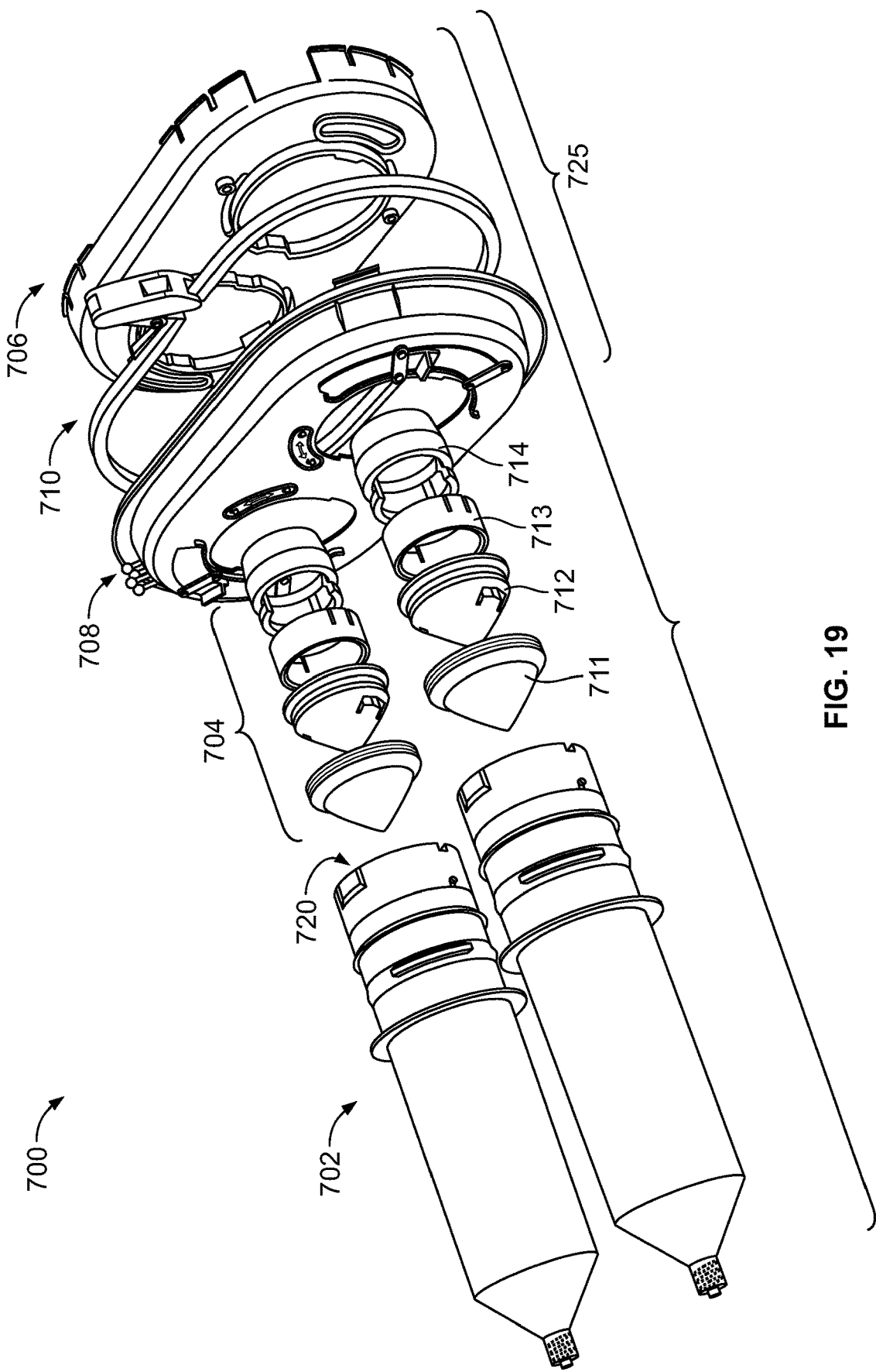
FIG. 19 is an exploded view of an injection sub-assembly formed in accordance with an embodiment.
Figure 20:
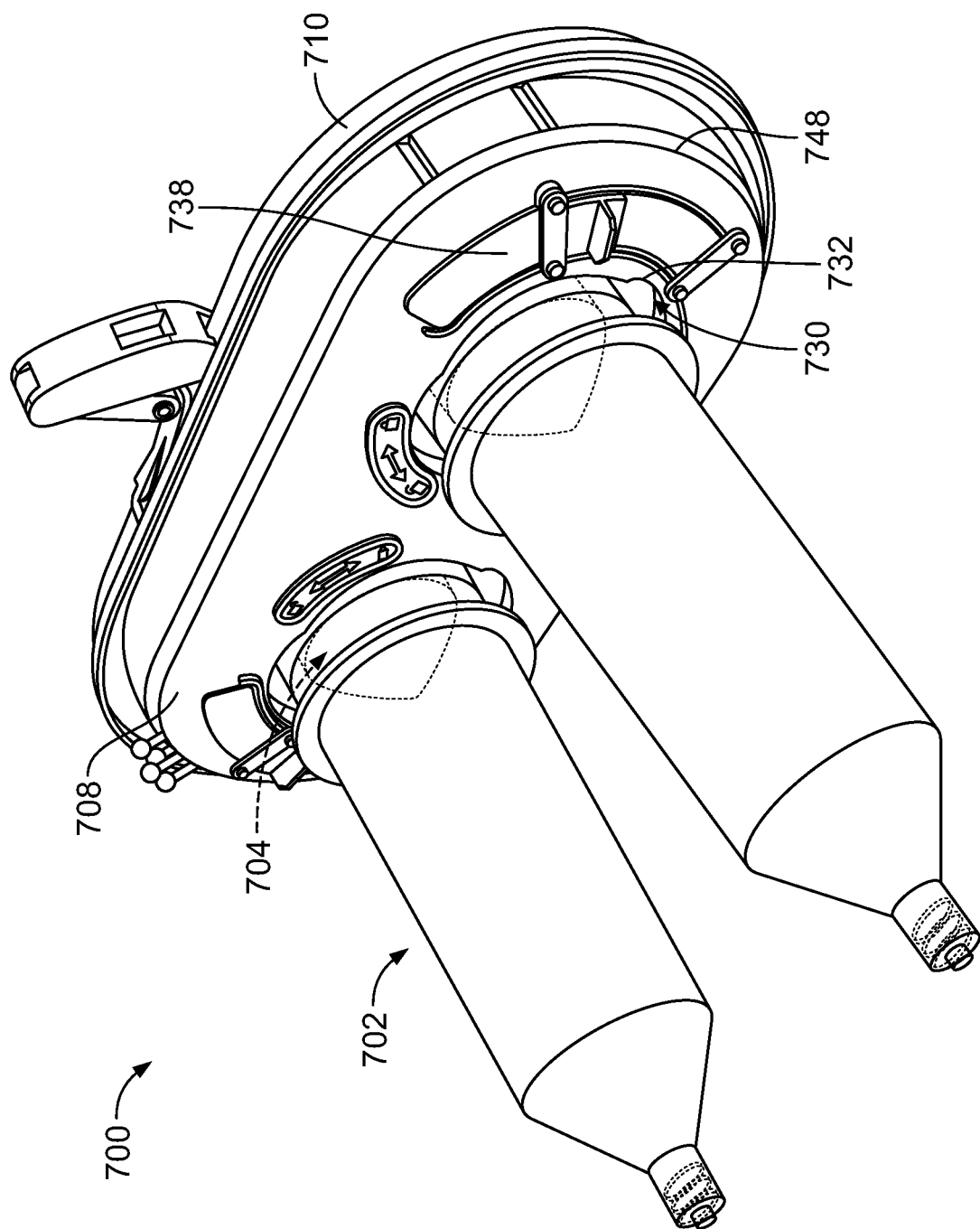
FIG. 20 is a front perspective view of the injection sub-assembly of FIG. 19.
Figure 21:
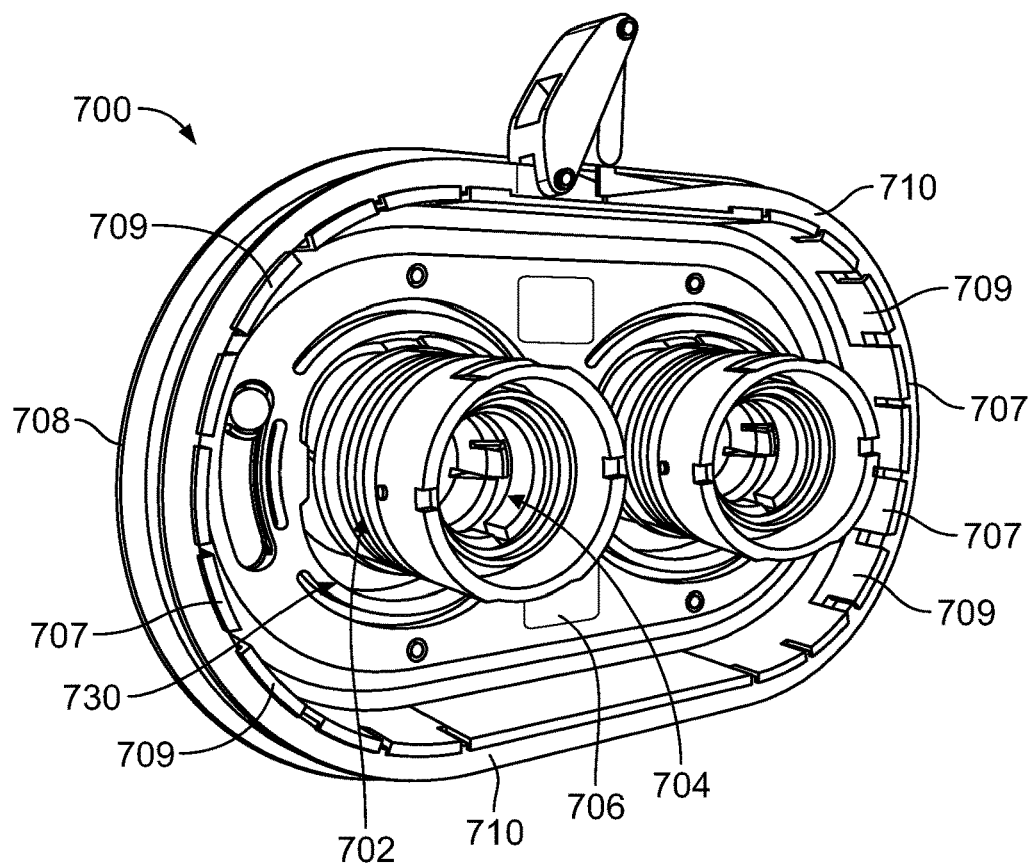
FIG. 21 is a rear perspective view of the injection sub-assembly FIG. 19.

FIGS. 19-21 illustrate an injection sub-assembly 700 formed in accordance with an embodiment. FIG. 19 is an exploded view of an injection sub-assembly 700 formed in accordance with an embodiment. As shown, the injection sub-assembly 700 includes syringe barrels 702, plunger assemblies 704, and a fascia 706. The syringe barrels 702 may be similar or identical to the other syringe barrels described herein. The fascia 706 may also be similar or identical to the other fascias described herein.

The injection sub-assembly 700 also includes a shroud 708 and a strap or belt 710. The shroud 708 is configured to cover the fascia 706. For example, the shroud 708 may cover tactile openings and switch openings to prevent ingress of leaked fluid. The shroud 708 may be removably coupled so that, for example, the shroud 708 may be washed separately and then mounted to the fascia 706 again.

The shroud 708, the strap 710, and the fascia 706 combine to form a side cover 725 that is configured to cover at least a portion of an active side of an injector head. In the illustrated embodiment, the side cover 725 is an assembly that includes three discrete elements. In other embodiments, the side cover may include only two elements (e.g., the shroud and fascia or the strap and one of the shroud or fascia). The side cover may include more than three elements. Yet in other embodiments, the side cover includes only the shroud 708 or only the fascia 706 or a similar element. For example, the fascia 604 may be referred to as a side cover. The shroud 708, the fascia 706, and the side cover 725 may also be referred to as a support structure of the magnetic switch 738. Accordingly, the term "side cover," when recited in the claims, includes a cover that is identical to or similar to a fascia or shroud.

Although the illustrated embodiment shows the injection sub-assembly 700 including the syringe barrels 702, the plunger assemblies 704, the shroud 708, the strap 710, and the fascia 706, other embodiments may include fewer or more components than those shown. For example, in some embodiments, the injection sub-assembly 700 may include only the fascia 706 and the shroud 708.

Each of the plunger assemblies 704 is configured to engage a distal end of a piston (not shown). As shown, the plunger assembly 704 includes a plunger cover 711, an internal member 712, and piston connectors 713, 714. The plunger cover 711, the internal member 712, and the piston connectors 713, 714 may be stacked together and inserted through a load opening 720 of the corresponding syringe barrel 702.

FIG. 20 is a front perspective view of the injection sub-assembly 700, and FIG. 21 is a rear perspective view of the injection sub-assembly 700. As shown, the shroud 708 and, optionally, the strap 710 may be configured to essentially cover an entirety of the fascia 706, except for syringe openings 730 (also shown in FIG. 19). The shroud 708 includes shroud openings 732 (FIG. 20) that align with the syringe openings 730.

The fascia 706 has a contoured body that is configured to extend over and cover the injector head. The fascia 706 forms a bowl or basin 734 that receives a portion of the injector head. The shroud 708 has a similarly sized bowl or basin that receives the fascia 706. In some embodiments, the fascia 706 and the shroud 708 include grip extensions 707, 709, respectively. The grip extensions 707 are positioned along a perimeter of the fascia 706. The grip extensions 707 are positioned to form a plurality of gaps 736 where the grip extensions 709 of the shroud 708 are positioned. As such, the grip extensions may be evenly distributed about the injector head when coupling to the injector head. In alternative embodiments, the shroud 708 does not coupled directly to the injector head. For example, the shroud may directly couple to the fascia 706.

When the injection sub-assembly 700 is fully constructed and the syringe barrel 702 is operably loaded, the retaining shoulders of the syringe barrel 702 are coplanar with the deflectable ribs of the fascia 706. In particular embodiments, the shroud 708 covers the deflectable ribs such that the retaining shoulders move between the injector head and the shroud 708 when the syringe barrel is turned. In other embodiments, the deflectable ribs may be covered by the shroud 708.

Figure 22:
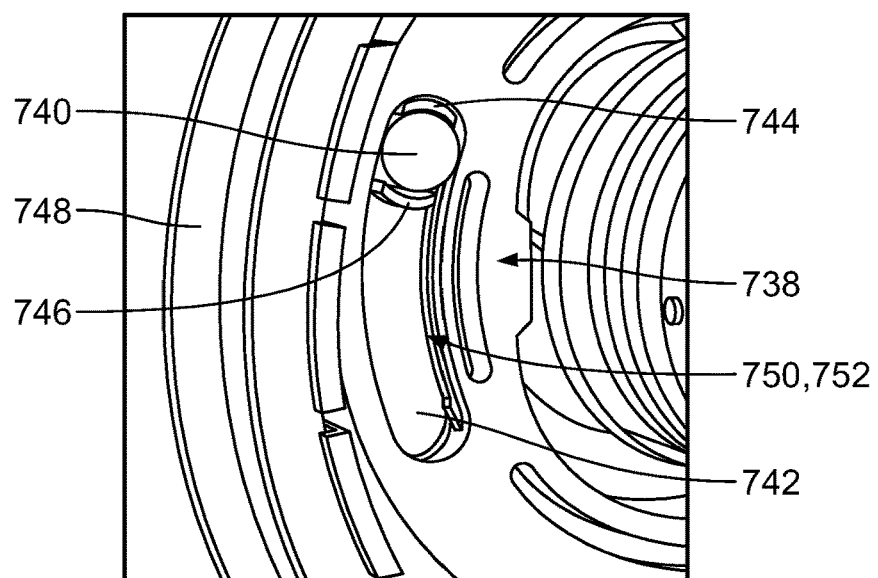
FIG. 22 is an enlarged view of an underside of the injection sub-assembly of FIG. 19.

FIG. 22 is an enlarged view of an underside of the injection sub-assembly 700. The injection sub-assembly 700 also includes a magnetic switch 738 (also shown in FIG. 20) that may be similar to the magnetic switches 120, 620. The magnetic switch 738 includes an external magnet 740 and a movable switch body 742 that is coupled to and carries the external magnet 740. In the illustrated embodiment, the external magnet 740 is a permanent magnet. In other embodiments, the magnetic switch 738 includes an electromagnet. The magnetic switch 738 and the external magnet 740 are positioned outside of the injector head in the illustrated embodiment. For example, the external magnet 740 may be immediately adjacent to the injector head such that the external magnet 740 engages the injector head or has only a nominal gap therebetween (e.g., less than 5 millimeters). It is contemplated, however, that the external magnet 740 may be located further away from the injector head. Other magnetic switches described (e.g., the magnetic switches 120, 620) herein may be operate in a similar manner as the magnetic switch 738.

The external magnet 740 is operable to modify a magnetic field experienced by the internal sensor to activate the internal sensor. In some embodiments, the movable switch body is a slider that is configured to slide along the fascia 706. In other embodiments, the movable switch body may be a toggle switch, rocker switch, or push-button switch(es). The movable switch body 742 may include first and second arms 744, 746 that engage and grip the external magnet 740. The movable switch body 742 is coupled to a body 748 of the shroud 708 and is configured to slide about the shroud opening 732. The magnet 740 and the arms 744, 746 extend through aligned slots 750, 752 of the shroud 708 and the fascia 706, respectively. The magnet 740 may slide through the slots 750, 752 when the movable switch body 742 is moved by a user. The slots 750, 752 may combine to form a track. In the illustrated embodiment, the track is arc-shaped that extends along the syringe opening. The slots 750, 752 may be configured (e.g., sized, shaped, and positioned) so that the external magnet 740 is above the sensor at a designated position within the track. For example, a mid-point along the track may correspond to the magnet 740 being above the sensor.

In some embodiments, however, the sensor may also be magnetically influenced by an internal magnet that is movable within the injector head. For example, the flex ring 226 (FIG. 3) is coupled to the internal permanent magnet 227 (FIG. 5) that is movable. For such embodiments when the injector head includes the internal magnet 227 (or similar movable, internal permanent magnet), the magnetic switch is configured to account for the magnetic field generated by the internal magnet.

In an alternative embodiment, the injection sub-assembly 700 does not include the shroud 708 or the fascia 706 but does include the magnetic switch 738. In such embodiments, a support structure may hold the magnetic switch. For example, a housing of the magnetic switch may be adhered to a side, such as the active side or other side, of the injector head.

Figure 23:
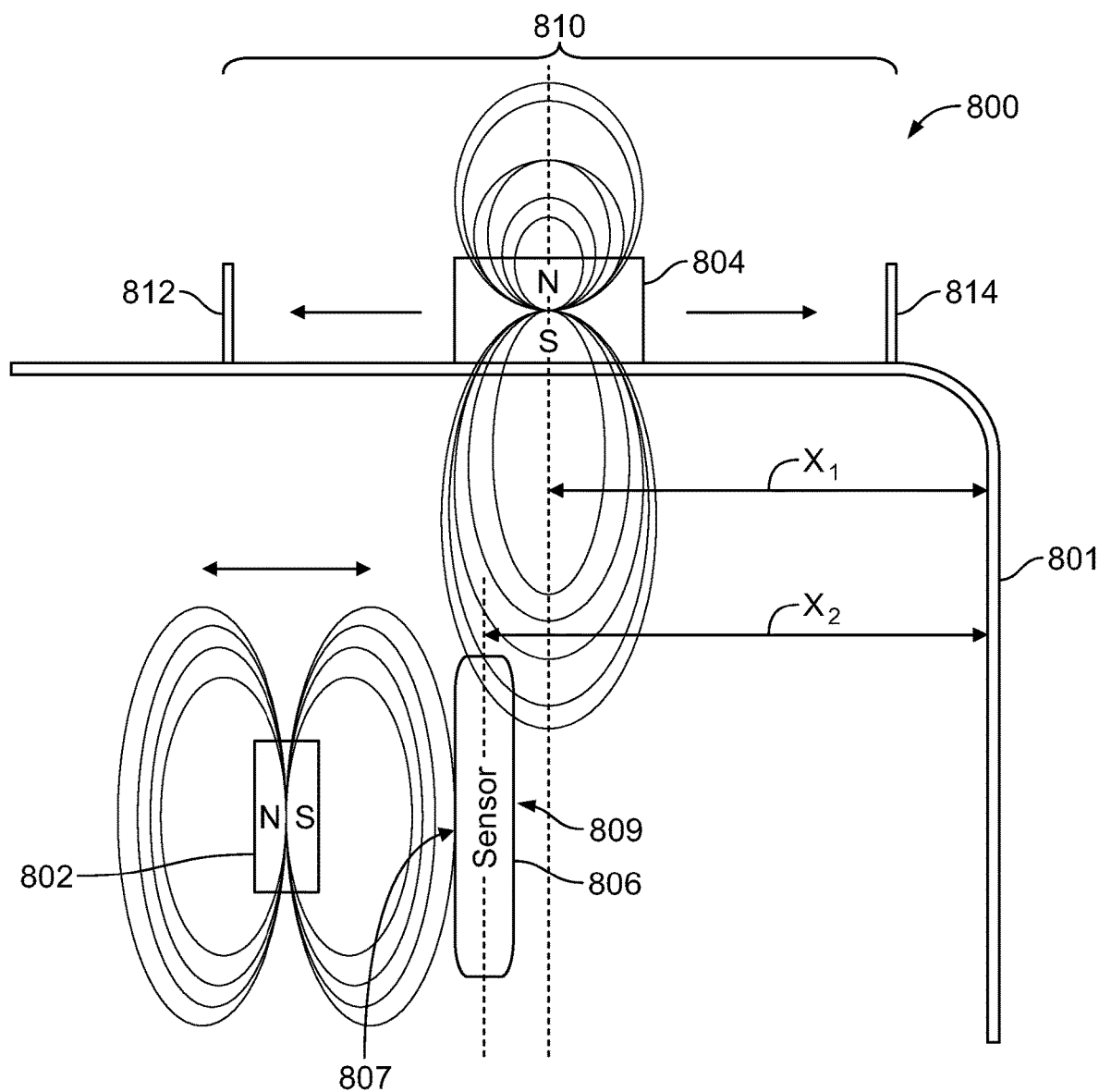
FIG. 23 is a schematic diagram of a magnetic switch and illustrates the magnetic influence of an internal magnet and an external permanent magnet on an internal sensor of an injector head.

FIG. 23 is a schematic diagram illustrating the magnetic influence of an internal magnet 802 and an external magnet 804 on an internal sensor 806. The external magnet 804 is part of a magnetic switch 800. The internal magnet 802 and the internal sensor 806 are positioned within an injector head 801. The influence of the external magnet 804 on the internal sensor 806 may be controlled by designating a range of relative positions of the external magnet 804. For example, the external magnet 804 may be movable along a track or slot such that the external magnet 804 will remain within a plane of the track but be capable of having different positions within the slot. As indicated in FIG. 23, the external magnet 804 may be moved between two different ends 812, 814 within a track 810.

Although illustrated embodiments have shown the magnetic switch being positioned along an active side from which the syringe barrels extend, other embodiments may include the magnetic switch at a different position. For example, the magnetic switch 800 or the external magnet 804 may be positioned along an outer side that extends vertically with respect to the horizontal active side.

A total magnetic influence on the internal sensor 806 may also be affected by a position of the internal magnet 802. As described herein, although the internal magnet 802 may be capable of moving relative to the internal sensor 806, at least some embodiments may avoid moving the internal magnet 802 by more than a negligible amount. For example, the syringe barrel may not engage the flex ring that holds the internal magnet 802.

The internal and external magnets 802, 804 have respective magnetic fields 803, 805. In FIG. 23, the magnetic field 805 of the external magnet 804 aligns with a back side 809 of the internal sensor 806, and the magnetic field 803 of the internal magnet 802 aligns with a front side 807 of the internal sensor 806. The magnetic fields 803, 805 are caused by the South poles of the respective magnets in the illustrated embodiment, but may be caused by the North poles of the respective magnets in other embodiments. Yet in other embodiments, the magnetic fields 803, 805 may be caused by different poles.

In FIG. 23, the internal and external magnets 802, 804 are positioned such that the internal sensor 806 indicates the syringe is present (e.g., operably engaged to the injector head). Without the external magnet 804, however, the position of the internal magnet 802 would cause the internal sensor 806 to indicate the syringe is not present. More specifically, the designated position of the external magnet 804 has the same effect as moving the internal magnet 802 away from the internal sensor 806. In other words, the magnetic field 805 reduces the strength of the magnetic field 803, thereby causing the circuitry of the internal sensor 806 to indicate a syringe is present. If the external magnet 804 were moved further away from the back side 809 of the internal sensor 806, the total magnetic field experience by the circuitry of the internal sensor 806 would increase because the strength of the magnetic field 805 is decreased. If the external magnet 804 were moved to the front side 807 of the internal sensor 806, however, the total magnetic field experienced by the circuitry of the internal sensor 806 would increase because the strength of the magnetic field 805 is added to the strength of the magnetic field 803. Accordingly, the external magnet 804 may be moved in either direction to increase the total magnetic field experienced by the circuitry of the internal sensor 806 and cause the internal sensor 806 to indicate that the syringe is not present.

Figure 24:
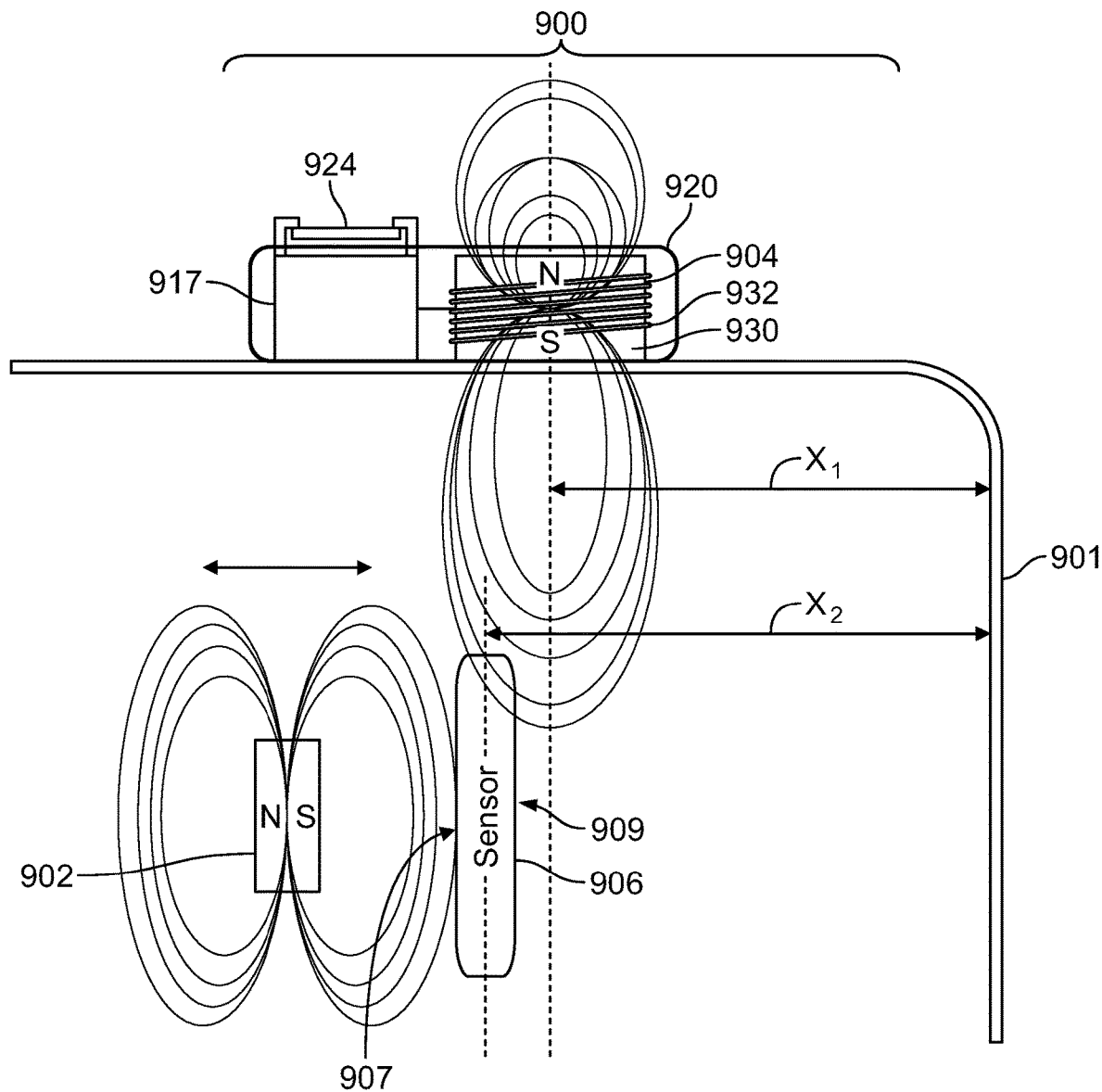
FIG. 24 is a schematic diagram of a magnetic switch and illustrates a magnetic influence of an internal magnet and an external electromagnet on an internal sensor of an injector head.

FIG. 24 is a schematic diagram of a magnetic switch 900 and illustrates a magnetic influence of an internal magnet 902 and an external magnet 904 on an internal sensor 906. The external magnet 904 is operable to modify a magnetic field experienced by the internal sensor 906 to activate the internal sensor 906. The magnetic switch 900 and the external magnet 904 are positioned outside of the injector head 901. The external magnet 904 may be immediately adjacent to the injector head 901 such that the external magnet 904 engages the injector head 901 or has only a nominal gap therebetween (e.g., less than 5 millimeters). It is contemplated, however, that the external magnet may be located further away from the injector head 901. Other magnetic switches described (e.g., the magnetic switches 120, 620, and 738) herein may be configured to operate in a similar manner as the magnetic switch 900.

The magnetic switch 900 includes the external magnet 904, a power source 917, a support structure 920, and a button 924. In FIG. 24, the external magnet 904 is an electromagnet having a core 930 and a conductor 932 that is wrapped about the core 930. The conductor 932 is electrically coupled to the power source 917 (e.g., battery). The power source 917 may be activated when, for example, a user presses the button 924. The button 924 is coupled to the support structure 920. In FIG. 24, the support structure 920 is a housing of the magnetic switch 900. In other embodiments, however, the support structure may be a side cover, such as a shroud and/or a fascia as described herein. When the power source 917 is activated, the electromagnet generates a respective magnetic field that affects the total magnetic field experienced by the internal sensor.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

What is claimed is:

1. A syringe barrel comprising:
a barrel body having a passage extending along a longitudinal axis between a tip opening and a load opening, the passage configured to permit a plunger to advance therethrough along the longitudinal axis for driving a liquid through the tip opening; and
wherein the barrel body includes a base portion that is configured to operably engage an injection system, the base portion having a body surface that is shaped to form a light-propagating space positioned along a first arcuate section of the body surface that does not extend entirely around the base portion, wherein the light-propagating space is recessed into the body surface toward the longitudinal axis of the barrel body, wherein the light-propagating space includes a light-propagating recess defined between side surfaces recessed into the body surface, the light-propagating space being defined by reflective ramps of the body surface, the reflective ramps having predetermined sizes and positions to reflect light signals radially away from the barrel body.

2. The syringe barrel of claim 1, wherein the base portion has a load edge that defines the load opening, the load edge having a reduced thickness along the light-propagating recess, the light-propagating recess extending from the load edge to the reflective ramps.

3. The syringe barrel of claim 2, wherein the body surface is an exterior surface.

4. The syringe barrel of claim 1, wherein the base portion includes a base wall that has the body surface and a load edge that defines the load opening, the base portion being incapable of having an appreciable amount of electromagnetic radiation with a detectable wavelength propagate from the load edge through the base wall to the reflective ramps.

5. The syringe barrel of claim 4, wherein the base portion is incapable of having the appreciable amount of electromagnetic radiation with the detectable wavelength propagate from the load edge through the base wall to the reflective ramps because of at least one of the following:
(a) the base portion is shaped from an opaque material;
(b) the body surface of the base portion is coated with an opaque material; and
(c) the base portion includes discontinuities therein that scatter the electromagnetic radiation.

6. The syringe barrel of claim 1, wherein the light-propagating space is defined by at least first and second levels of the body surface.

7. The syringe barrel of claim 1, wherein the light-propagating space is a first light-propagating space and the reflective ramps are first reflective ramps, the barrel body being shaped to form a second light-propagating space positioned along a second arcuate section of the body surface and defined by second reflective ramps of the body surface, the second reflective ramps having predetermined sizes and positions to reflect light signals radially away from the barrel body.

8. The syringe barrel of claim 7, wherein the first and second light-propagating spaces are located on opposite sides of the barrel body or on opposite sides of a wall of the barrel body.

9. The syringe barrel of claim 1, wherein the barrel body also includes a main portion, the main portion and the base portion being discrete elements that are attached to each other to form the barrel body.

10. The syringe barrel of claim 9, wherein:
one of the main portion and the base portion has an edge channel that extends circumferentially around the longitudinal axis and opens in a direction along the longitudinal axis, the edge channel being defined between an inner wall and an outer wall; and
the other of the main portion and the base portion having an edge track that extends circumferentially around the longitudinal axis, the edge track configured to be received within the edge channel and threadably engaging each other such that the edge track is secured between the inner wall and the outer wall that define the edge channel.

11. The syringe barrel of claim 1, wherein the light-propagating space does not extend radially outward from an outer surface of the body surface or the base portion.

12. A syringe-confirmation assembly comprising:
a syringe barrel having a passage extending along a longitudinal axis between a tip opening and a load opening, the passage configured to permit a plunger to advance therethrough along the longitudinal axis for driving a liquid through the tip opening, wherein the syringe barrel includes a base portion that is configured to operably engage an injection system, the base portion having a body surface that is shaped to form a light-propagating space alongside the base portion, wherein the light-propagating space is recessed into the body surface toward the longitudinal axis of the syringe barrel, wherein the light-propagating space includes a light-propagating recess defined between side surfaces recessed into the body surface; and
a light source configured to generate light, the light source being positioned to direct the light through the light-propagating space alongside the body surface, wherein the base portion includes reflective ramps positioned along a first arcuate section of the base portion that does not extend entirely around the base portion, wherein the reflective ramps are recessed into the body surface toward the longitudinal axis of the syringe barrel, the reflective ramps having predetermined sizes and positions to reflect light signals radially away from the syringe barrel.

13. The syringe-confirmation assembly of claim 12, wherein the light comprises electromagnetic radiation having a designated wavelength or a designated range of wavelengths.

14. The syringe-confirmation assembly of claim 12, wherein the side surfaces partially oppose each other with the light-propagating space therebetween.

15. The syringe-confirmation assembly of claim 12, wherein the base portion has a load edge that defines the load opening, the load edge having a reduced thickness along the light-propagating space.

16. The syringe-confirmation assembly of claim 12, wherein the light-propagating space is defined by at least first and second levels of the body surface.

17. The syringe-confirmation assembly of claim 12, wherein the base portion includes a base wall that has the body surface and a load edge that defines the load opening, the base portion being incapable of having an appreciable amount of electromagnetic radiation with a detectable wavelength propagate from the load edge through the base wall to the reflective ramps.

18. The syringe-confirmation assembly of claim 17, wherein the base portion is incapable of having the appreciable amount of electromagnetic radiation with the detectable wavelength propagate from the load edge through the base wall to the reflective ramps because of at least one of the following:
(a) the base portion is shaped from an opaque material;
(b) the body surface of the base portion is coated with an opaque material; and
(c) the base portion includes discontinuities therein that scatter the electromagnetic radiation.

19. The syringe-confirmation assembly of claim 12, wherein the light-propagating space is a first light-propagating space and the reflective ramps are first reflective ramps, the syringe barrel being shaped to form a second light-propagating space that extends to second reflective ramps positioned along a second arcuate section of the base portion, the second reflective ramps having predetermined sizes and positions to reflect light signals radially away from the syringe barrel.

20. The syringe-confirmation assembly of claim 12, wherein the syringe barrel also includes a main portion, the main portion and the base portion being discrete elements that are attached to each other to form the syringe barrel.

* * * * *